(12) United States Patent
Minko et al.

(10) Patent No.: US 9,445,993 B2
(45) Date of Patent: Sep. 20, 2016

(54) NANOTECHNOLOGY APPROACH FOR INHALATION THERAPIES

(71) Applicant: Rutgers, The State University of New Jersey, New Brunswick, NJ (US)

(72) Inventors: Tamara Minko, Somerset, NJ (US); Olga B. Garbuzenko, Highland Park, NJ (US); Vera Ivanova, Franklin Park, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 649 days.

(21) Appl. No.: 13/863,828

(22) Filed: Apr. 16, 2013

(65) Prior Publication Data
US 2013/0273164 A1    Oct. 17, 2013

Related U.S. Application Data

(60) Provisional application No. 61/625,049, filed on Apr. 16, 2012.

(51) Int. Cl.
| | |
|---|---|
| *A61K 9/127* | (2006.01) |
| *A61K 31/5575* | (2006.01) |
| *A61K 31/355* | (2006.01) |
| *A61K 31/713* | (2006.01) |
| *A61K 9/00* | (2006.01) |
| *A61K 9/51* | (2006.01) |
| *A61K 47/48* | (2006.01) |

(52) U.S. Cl.
CPC ............ *A61K 9/127* (2013.01); *A61K 9/0078* (2013.01); *A61K 9/5123* (2013.01); *A61K 31/355* (2013.01); *A61K 31/5575* (2013.01); *A61K 31/713* (2013.01); *A61K 47/48815* (2013.01)

(58) Field of Classification Search
CPC ...................................... A61K 9/127
See application file for complete search history.

(56) References Cited

U.S. PATENT DOCUMENTS

| | | | | |
|---|---|---|---|---|
| 5,925,375 | A * | 7/1999 | Lenk ...................... | A61K 9/127 424/450 |
| 2002/0182248 | A1* | 12/2002 | Yamauchi ............ | A61K 9/1272 424/450 |
| 2003/0212139 | A1* | 11/2003 | Neal ..................... | A61K 9/0034 514/573 |
| 2008/0082168 | A1* | 4/2008 | Peterman ................ | A61F 2/442 623/17.11 |
| 2009/0163450 | A1* | 6/2009 | Hoffmann .......... | A61K 31/5578 514/161 |
| 2009/0324698 | A1* | 12/2009 | Wagner ................ | A61K 9/0034 424/450 |
| 2012/0177723 | A1* | 7/2012 | Torchilin .............. | C12N 15/111 424/450 |

\* cited by examiner

*Primary Examiner* — Gollamudi Kishore
(74) *Attorney, Agent, or Firm* — Fox Rothschild LLP

(57) ABSTRACT

This invention relates to lipid nanoparticle compositions and methods for the localized delivery of active agents via inhalation therapy.

12 Claims, 14 Drawing Sheets

Figures 8A-E
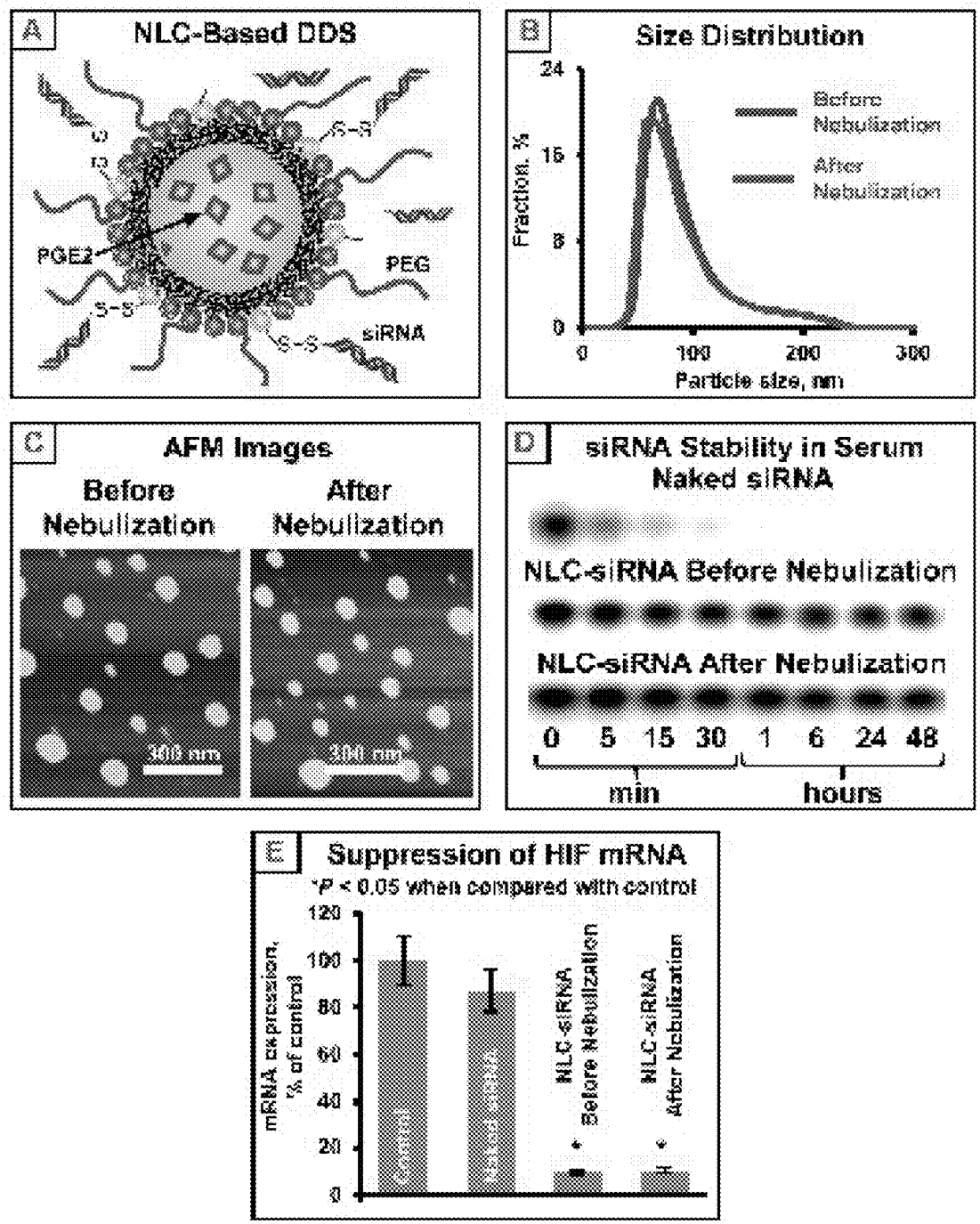

Figures 9A-E
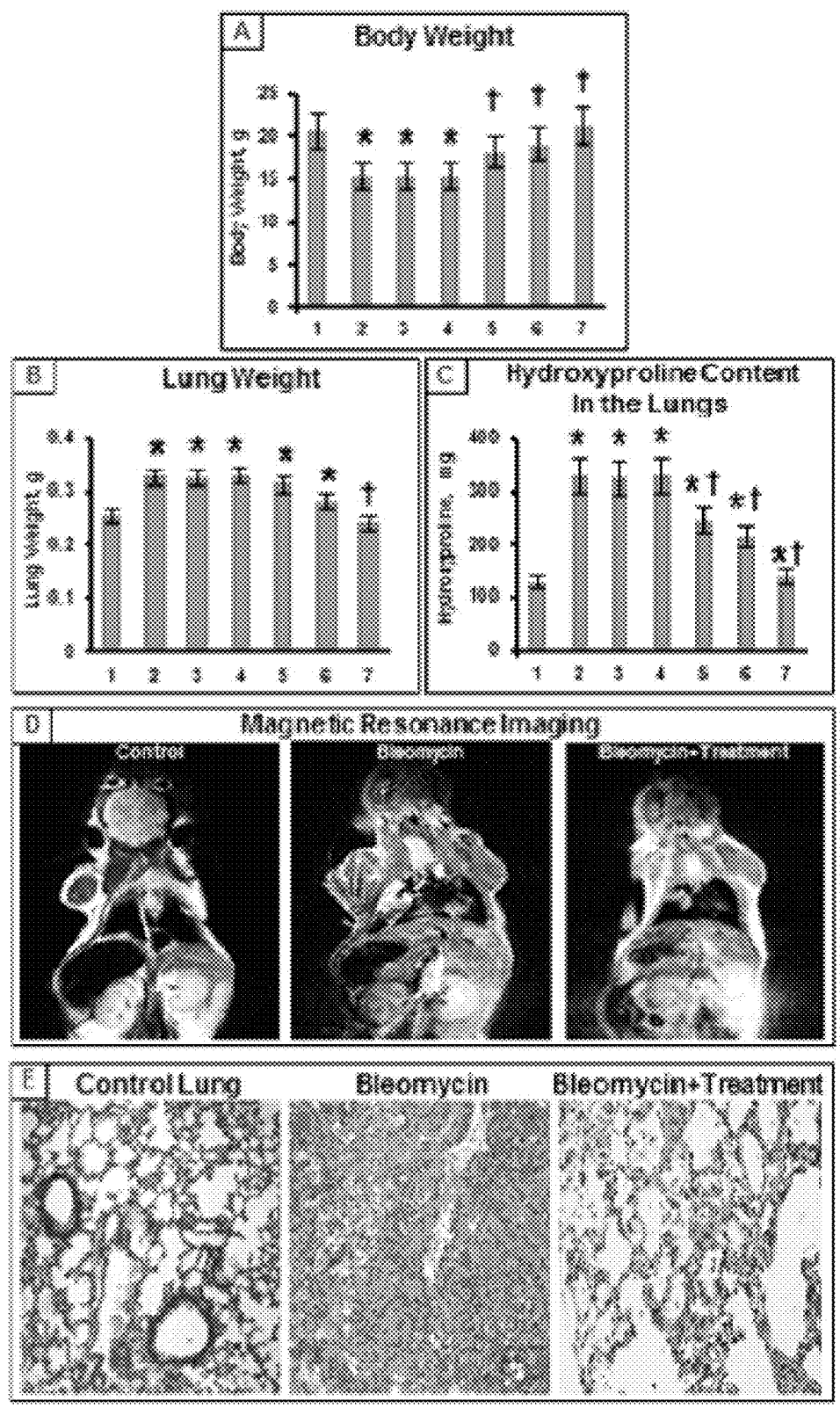

Figures 10A-B
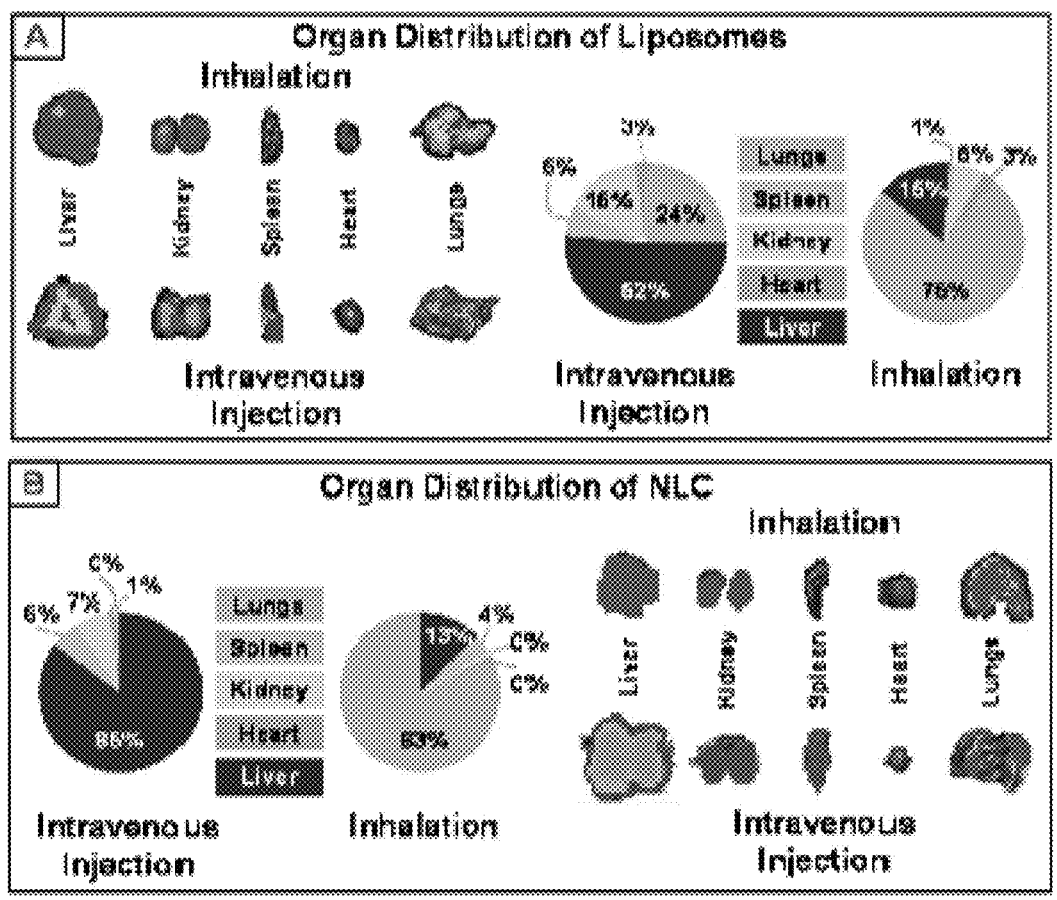

Figures 11A-C
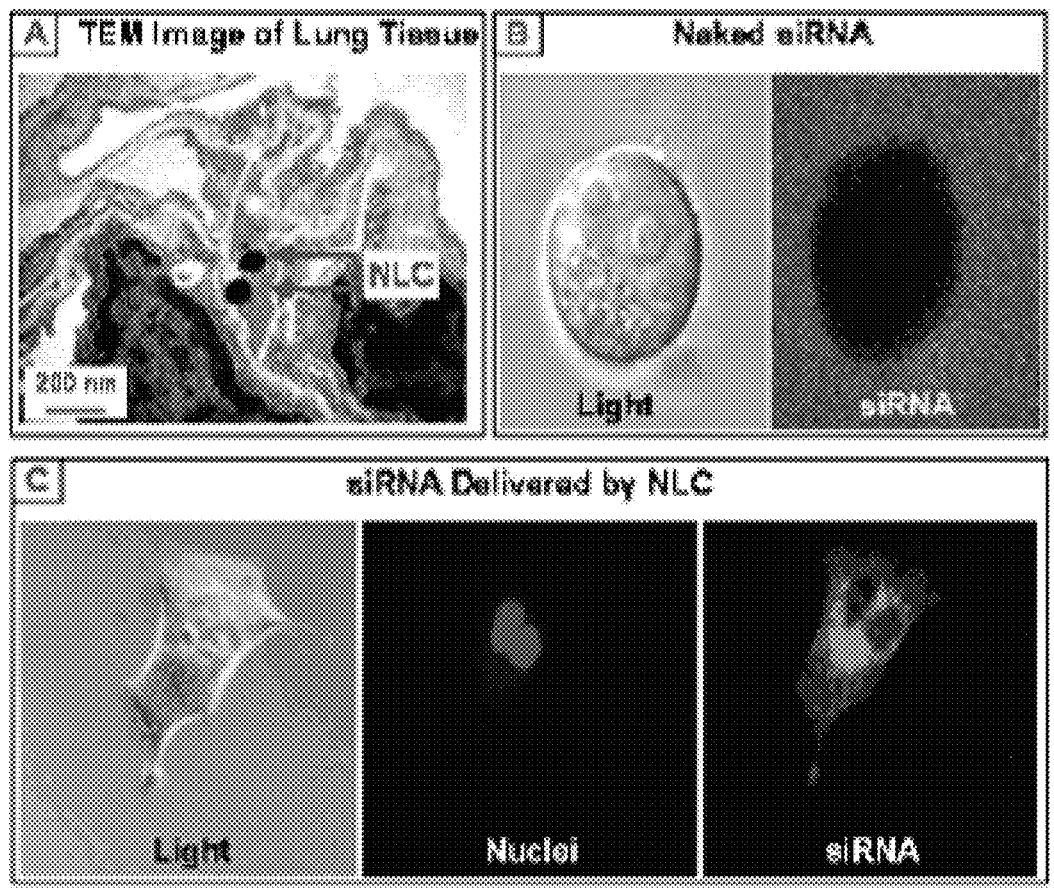

Figures 13A-B
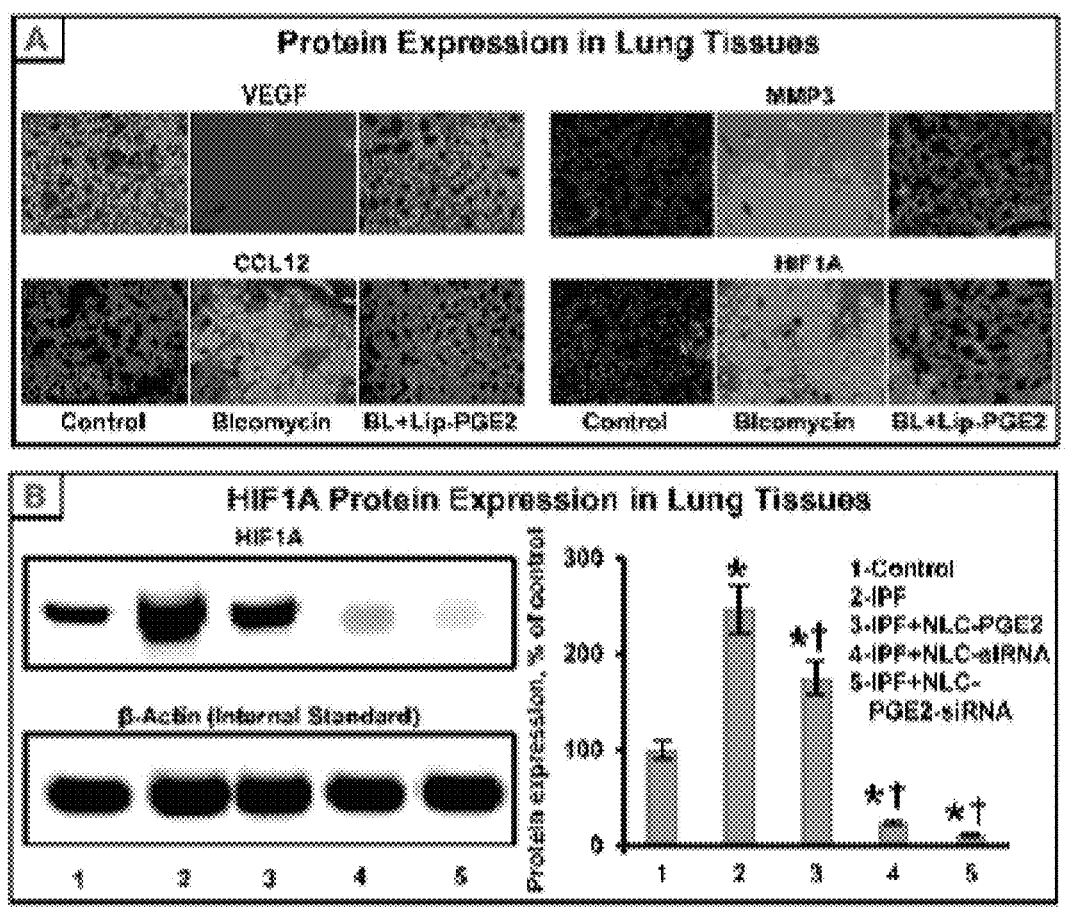

NANOTECHNOLOGY APPROACH FOR INHALATION THERAPIES

CROSS-REFERENCE TO RELATED APPLICATIONS

This application claims the benefit of U.S. Provisional Application No. 61/625,049, filed Apr. 16, 2012, the contents of which are hereby incorporated by reference in their entirety.

GOVERNMENT LICENSE RIGHTS

The present invention was made, at least in part, with government support under grant numbers NIH R01 CA111766 and NIH ES-0050 awarded by the National Institutes of Health. The government has certain rights in the invention.

BACKGROUND

Idiopathic pulmonary fibrosis (IPF) is a chronic, progressive, and often fatal form of interstitial lung disease. IPF is the most common form of idiopathic interstitial pneumonias. IPF causes the loss of lung epithelial cells, replacement of normal functional tissue, accumulation of fibroblasts and myofibroblasts, extracellular matrix deposition, alteration of lung architecture, pulmonary hypertension leading to substantial impairment of respiration and gas exchange often resulting in patient morbidity and mortality.

Treatment of IPF represents a major clinical challenge since this disorder does not have reliable therapeutic options and an effective therapy has yet to be identified and developed. Patient may ultimately require supportive oxygen therapy or pulmonary transplantation. Consequently, the development of a novel effective treatment of this devastating disease represents a very important and urgent task.

Prostaglandin E2 (PGE2), a cyclooxygenase-derived lipid mediator, has attracted considerable attention for its role in the development and progression of IPF and as a possible therapeutic for this disease. A role for PGE2 in the treatment of IPF is based on the very specific and unique role that PGE2 plays in the lungs making "the lung as a privileged site for the beneficial actions of PGE2." In other organs and tissues, PGE2 often acts as a potent pro-inflammatory mediator and is involved in pathogenesis of many inflammatory diseases. In contrast, in the lungs, PGE2 limits the immune-inflammatory response, inhibits specific lung fibroblast functions, their proliferation and synthesis of matrix proteins such as collagen. Consequently, PGE2 potentially can be used for the treatment of IPF. Moreover, it was recently shown that a synthetic analog of PGE2 (16,16-dimethyl-PGE2) recently was tested using in a model of pulmonary fibrosis (intratracheal administration of bleomycin) with promising results for treatment of IPF.

Systemic delivery of PGE2 has several limitations including the short half-life in the blood stream, low accumulation in the lungs and possible adverse side effects on other organs and tissues. In contrast, local inhalation delivery of PGE2 directly to the lungs has the potential to enhance the treatment of IPF (or other pulmonary conditions, such as, pulmonary fibrosis, interstitial lung disease, idiopathic interstitial pneumonia, and asthma) by increasing its local pulmonary concentration and preventing (or at least limiting) its penetration into the bloodstream and distribution to other healthy organs. However, free native PGE2 cannot be delivered into the lungs by inhalation requiring a special dosage form or delivery system that can be inhaled. Accordingly, there is a need to allow delivery of PGE2 into the lungs.

SUMMARY

This document describes compositions and methods for pulmonary (inhalation) delivery of one or more active agents that improve the stability and solubility of the active agent(s), provide carriers with low cyto- and genotoxicity, enhances content of the active agent(s) in the lungs, achieve better penetration into cells, provide for greater biocompatibility, avoid the use of organic solvents for the preparation of the lipid nanostructures, decrease the cost of dosage form, and simplify scale-up and sterilization procedures.

There is provided in accordance with various embodiments a composition that includes a plurality of lipid nanoparticles, wherein at least one lipid nanoparticle includes: (i) a lipid membrane surrounding an inner compartment of the nanoparticle, (ii) an aqueous phase encapsulated by the inner compartment, and (iii) at least one water-soluble active agent contained within the aqueous phase, wherein the active agent is selected from water-soluble prostaglandins, water-soluble prostaglandin analogues, water-soluble antioxidants, and combinations thereof, wherein each lipid nanoparticle has a diameter ranging from 1 nm to 1000 nm.

Also provided is a composition that includes a plurality of lipid nanoparticles, wherein at least one lipid nanoparticle includes: (i) a mixture of solid and liquid lipids and (ii) at least one lipid-soluble active agent contained within the lipid mixture, wherein the active agent is selected from lipid-soluble prostaglandins, lipid-soluble prostaglandin analogues, lipid-soluble antioxidants, and combinations thereof, wherein each lipid nanoparticle has a diameter ranging from 1 nm to 1000 nm.

In one embodiment, the active agent is water-soluble prostaglandin E2. In another embodiment, the active agent is lipid-soluble α-tocopherol.

In an additional embodiment, the composition includes, in combination with the plurality of lipid nanoparticles, one or more pharmaceutical excipients selected from humectants, viscosity modifiers, surfactants, pH stabilizers, freeze drying protectants, polymers, and combinations thereof.

In another embodiment, the composition further includes one or more additional ingredients contained within the lipid nanoparticle or bound to an outer lipid surface of the lipid nanoparticle, wherein the one or more additional ingredients are selected from anti-histaminic agents, anti-inflammatory agents, corticosteroids, nucleic acids, peptides, proteins, oligonucleotides, enzyme imaging agents, fluorescent dyes and combinations thereof. In one embodiment, the additional ingredient is siRNA bound to the lipid nanoparticle via a cationic agent or bound to the lipid nanoparticle via a disulfide bond. In another embodiment, the additional ingredient is a cyclooxygenase inhibitor.

In yet another embodiment, the lipid nanoparticle further includes 1,2-distearoyl-sn-glycero-3-phosphoethanolamine-N-[amino(polyethylene glycol) bound to an outer lipid surface of the lipid nanoparticle. In an additional embodiment, the composition further includes siRNA bound to the lipid nanoparticle via a cationic agent or bound to an outer lipid surface of the lipid nanoparticle via a disulfide bond. In another embodiment, the lipid nanoparticle further includes cholesterol incorporated into the lipid membrane.

Also provided is a method for treating a pulmonary condition in a mammal by administering to the lungs of a mammal in need thereof a formulation, which includes a composition according to the present invention, wherein the pulmonary condition is selected from pulmonary fibrosis, interstitial lung disease, idiopathic interstitial pneumonia, and asthma.

In one embodiment, the active agent is a water-soluble prostaglandin and the lipid nanoparticle further includes 1,2-distearoyl-sn-glycero-3-phosphoethanolamine-N-[amino(polyethylene glycol) bound to an outer lipid surface of the lipid nanoparticle. In another embodiment, the active agent is a lipid-soluble prostaglandin and the lipid nanoparticle further includes 1,2-distearoyl-sn-glycero-3-phosphoethanolamine-N-[amino(polyethylene glycol) bound to an outer lipid surface of the lipid nanoparticle.

In yet another embodiment, the formulation used in the method includes siRNA bound to the lipid nanoparticle via a cationic agent or bound to an outer lipid surface of the lipid nanoparticle via a disulfide bond. In another embodiment, the formulation is delivered via a nebulizer.

BRIEF DESCRIPTION OF THE DRAWINGS

FIGS. 8A-E are related to nanostructured lipid carriers ((A) Structure of NLC-based DDS; (B) Particle size distribution by dynamic light scattering; (C) Atomic force microscope (AFM) images of nanoparticles; (D) Stability of siRNA in serum by EtBr replacement assay; and (E) Expression of targeted mRNA by quantitative RT-PCR;

FIGS. 9A-E depict validation of IPF model and inhalation treatment with PGE2 delivered by liposomes (Lip-PGE2) or NLC (NLC-PGE2 and NLC-PGE2-siRNA) ((A,B) Influence of inhalation (inhal.) and i.v. treatment of IPF with Lip-PGE2 or NLC-PGE2 on body and lung weight; (C) hydroxyproline content in the lungs (1—healthy animals (control); 2—animals with IPF (bleomycin); 3—animals with IPF treated with empty liposomes; 4—animals with IPF treated with empty NLC; 5—animals with IPF treated with Lip-PGE2; 6—animals with IPF treated with NLC-PGE2; 7—animals with IPF treated with NLC-PGE2-siRNA (targeted to HIF1A mRNA)); (D) representative MRI images of healthy mice and untreated and treated animals with fibrosis; and (E) lung tissue histology);

FIGS. 10A-B depict relative lung tissue content of liposomes (A) and NLC (B) delivered to mice by intravenous instillation or inhalation;

FIGS. 11A-C depict lung tissue and cellular internalization of NLC and siRNA. ((A) representative transmission electron microscope (TEM) image of lung tissue of healthy mouse treated with NLC labeled by osmium tetroxide and delivered by inhalation; (B,C) representative confocal microscope images of lung cells incubated with fluorescently labeled siRNA (green fluorescence). The cell nuclei were stained with DAPI nuclear dye (blue fluorescence);

FIGS. 13A-B show expression of VEGF, MMP3, CCL12, and HIF1A proteins (immunohistochemistry (A) and Western blotting (B)) in lung tissues. Mice were treated by inhalation with PGE2 delivered by liposomes (A) and with PGE2 and/or siRNA (targeted to HIF1A mRNA) delivered by NLC (B). 1—healthy animals (control); 2—animals with IPF (bleomycin); 3—animals with IPF treated with NLC-PGE2; 4—animals with IPF treated with NLC-siRNA (targeted to HIF1A mRNA); 5—animals with IPF treated with NLC-PGE2-siRNA (targeted to HIF1A mRNA)).

DETAILED DESCRIPTION

Figure 1:
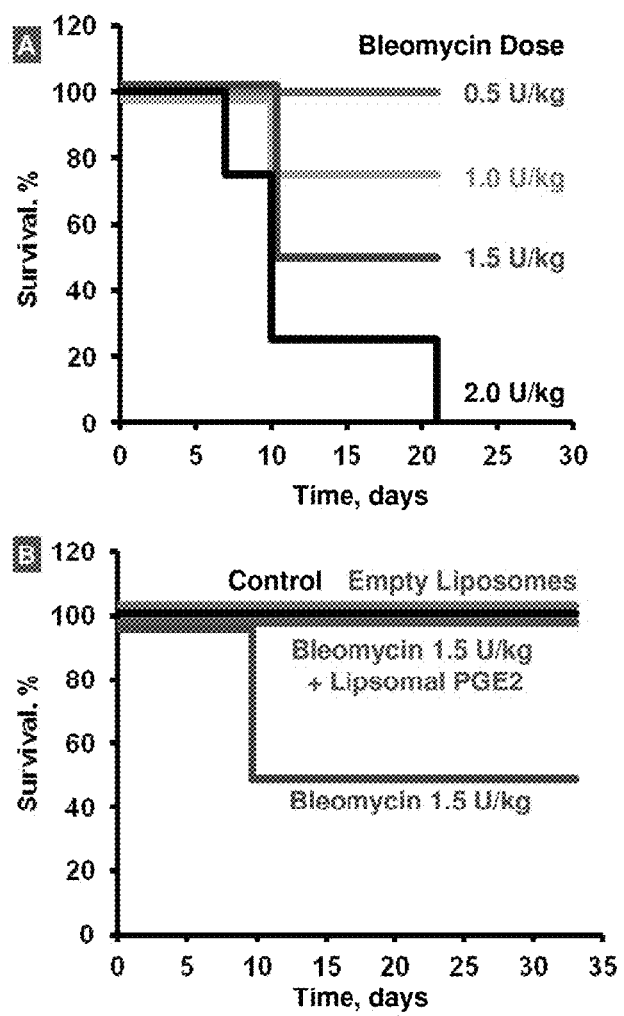
FIGS. 1A-B are plots showing % survival of mice after inhalation exposure to bleomycin ((A) Selection of bleomycin dose; (B) Inhalation treatment of mice with experimental lung fibrosis by liposomal PGE2 (Lip PGE2) prevents animal mortality)

This document describes compositions that include a plurality of lipid nanoparticles, wherein at least one lipid nanoparticle includes: (i) a lipid membrane surrounding an inner compartment of the nanoparticle, (ii) an aqueous phase encapsulated by the inner compartment, and (iii) at least one water-soluble active agent contained within the aqueous phase, wherein the active agent is selected from water-soluble prostaglandins, water-soluble prostaglandin analogues, water-soluble antioxidants, and combinations thereof, wherein each lipid nanoparticle has a diameter ranging from 1 nm to 1000 nm. Exemplary lipid nanoparticles falling within this description include liposomes.

In general, the term "liposome" includes within its meaning spherical amphiphilic compounds, including lipid compounds, typically in the form of one or more concentric layers. Amphiphilic compounds are those molecules having a hydrophilic polar head (e.g. a polar or ionic group) and a hydrophobic organic tail (e.g. a hydrocarbon chain). These compounds are generally also classified as surfactants, emulsifying agents or dispersing agents in the art.

Liposomes of the present invention are nanosized or in nanoparticle form having a size of no more than about 1000 nanometers. Exemplary liposomes described herein include multibinding nanoparticles no larger than about 250 nm, preferably about 50 nm to about 800 nm, more preferably about 100 nm to about 700 nm, and most preferably about 300 nm to about 650 nm.

Liposomes are typically formed in aqueous suspensions and contain at least one bilayer of an amphiphilic compound. The liposomes of the present invention encompass both unilamellar and multilamellar vesicles. In one embodiment, the hydrophilic heads of the amphiphilic compounds forming the external layer of the bilayer are directed towards the exterior of the spherical structure, while the hydrophilic heads of the amphiphilic compounds forming the internal layer of the bilayer are directed towards the interior of said spherical structure.

Optionally, at least one of the lipid nanoparticles includes one or more additional ingredients contained within the lipid nanoparticle (e.g. within an inner compartment and/or within a lipid membrane) or bound to an outer lipid surface of the lipid nanoparticle. Optional additional ingredients include anti-histaminic agents, anti-inflammatory agents, corticosteroids, nucleic acids, peptides, proteins, oligonucleotides, enzyme imaging agents, fluorescent dyes and combinations thereof. A preferred additional ingredient is a cyclo-oxygenase inhibitor. Preferably, lipid-soluble ingredients are contained within the lipid membrane and water-soluble ingredients are contained within the inner compartment dissolved or dispersed in an aqueous phase contained therein. One of skill in the art can readily modify the lipid or water solubility of an additional ingredient.

The liquid portion of the aqueous phase encapsulated by the inner compartment of the spherical structure of the liposomes is in general the same as the aqueous suspension. Optionally, the liquid portion of the aqueous phase includes one or more additional ingredients which are not present (or are present to a lesser extent) in the outer aqueous suspension, such as a water-soluble ingredient selected from water-soluble anti-histaminic agents, water-soluble anti-inflammatory agents, water-soluble corticosteroids, water-soluble nucleic acids, water-soluble peptides, water-soluble proteins, water-soluble oligonucleotides, water-soluble enzyme imaging agents, water-soluble fluorescent dyes and combinations thereof, or fewer ingredients than are present in the outer aqueous suspension. In at least one aspect of the present invention, the aqueous phase fills the internal volume of liposomes for the substantial totality of said volume, i.e. more than 90%, preferably more than 95% and typically for about 100%.

In one embodiment, the one or more additional ingredients are present in the liposome-forming composition, without necessarily being involved (or being only partially involved) in the formation of the liposomal envelope. These include pH regulators, osmolality adjusters, viscosity enhancers, emulsifiers, bulking agents, and combinations thereof and may be used in conventional amounts.

The liposomes described herein can optionally include one or more additional ingredients bound to an outer lipid surface of the lipid nanoparticle. Preferably, these ingredients are bound to a lipid nanoparticle having an overall net positive or negative charge via an anionic or cationic agent, respectively, or are covalently bound to the outer lipid surface of the lipid nanoparticle. Optional additional ingredients include anti-histaminic agents, anti-inflammatory agents, corticosteroids, nucleic acids, peptides, proteins, oligonucleotides, enzyme imaging agents, fluorescent dyes and combinations thereof. One of skill in the art can readily modify an additional ingredient having a neutral overall charge to possess an overall negative or positive charge complementary to the overall charge of the lipid nanoparticle. Additionally, one of skill in the art can, if necessary, readily modify an additional ingredient to enable it to bond covalently with the outer lipid surface via a linker group. Exemplary linker groups include, but are not limited to, a disulfide bond (S—S), an amino group ($NH_2$), and NHS ester crosslinkers.

In one embodiment, the additional active ingredient is siRNA bound to the lipid nanoparticle via a cationic agent or bound to the lipid nanoparticle via a disulfide bond.

In another embodiment, the lipid nanoparticle includes 1,2-distearoyl-sn-glycero-3-phosphoethanolamine-N-[amino(polyethylene glycol)] bound to an outer lipid surface of the lipid nanoparticle and optionally includes siRNA bound to the lipid nanoparticle via a cationic agent or bound to an outer lipid surface via a disulfide bond.

Also presented are compositions that include a plurality of lipid nanoparticles, wherein at least one lipid nanoparticle includes: (i) a mixture of solid and liquid lipids and (ii) at least one lipid-soluble active agent contained within the lipid mixture, wherein the active agent is selected from lipid-soluble prostaglandins, lipid-soluble prostaglandin analogues, lipid-soluble antioxidants, and combinations thereof, wherein each lipid nanoparticle has a diameter ranging from 1 nm to 1000 nm. Exemplary lipid nanoparticles falling within this description include nanostructured lipid carriers (NLCs). In general, NLCs are prepared by mixing solid and liquid lipid materials, such as those described below.

In one embodiment, one or more additional ingredients are optionally present in the NLC-forming composition. These include pH regulators, osmolality adjusters, viscosity enhancers, emulsifiers, bulking agents, and combinations thereof and may be used in conventional amounts.

Optionally, at least one of the lipid nanoparticles includes one or more additional ingredients contained within the lipid nanoparticle (e.g. within the mixture of solid and liquid lipids) or bound to an outer lipid surface of the lipid nanoparticle. Optional additional ingredients include anti-histaminic agents, anti-inflammatory agents, corticosteroids, nucleic acids, peptides, proteins, oligonucleotides, enzyme imaging agents, fluorescent dyes and combinations thereof. A preferred additional ingredient is a cyclo-oxygenase inhibitor. Preferably, lipid-soluble ingredients are contained within the lipid mixture. One of skill in the art can readily modify the lipid solubility of an additional ingredient.

The NLC lipid nanoparticles described herein can optionally include one or more additional ingredients bound to an outer lipid surface of the lipid nanoparticle. Preferably, these ingredients are bound to a lipid nanoparticle having an overall net positive or negative charge via an anionic or cationic agent, respectively, or are covalently bound to the outer lipid surface of the lipid nanoparticle. Optional additional ingredients include anti-histaminic agents, anti-inflammatory agents, corticosteroids, nucleic acids, peptides, proteins, oligonucleotides, enzyme imaging agents, fluorescent dyes and combinations thereof. One of skill in the art can readily modify an additional ingredient having a neutral overall charge to possess an overall negative or positive charge complementary to the overall charge of the lipid nanoparticle. Additionally, one of skill in the art can, if necessary, readily modify an additional ingredient to enable it to bond covalently with the outer lipid surface via a linker group. Exemplary linker groups include, but are not limited to, a disulfide bond (S—S), an amino group ($NH_2$), and NHS ester crosslinkers.

In one embodiment, the additional active ingredient is siRNA bound to the lipid nanoparticle via a cationic agent or bound to the lipid nanoparticle via a disulfide bond.

In another embodiment, the lipid nanoparticle includes 1,2-distearoyl-sn-glycero-3-phosphoethanolamine-N-[amino(polyethylene glycol)] bound to an outer lipid surface of the lipid nanoparticle and optionally includes siRNA bound to the lipid nanoparticle via a cationic agent or bound to an outer lipid surface via a disulfide bond.

In at least one embodiment, the materials used for preparing the lipid nanoparticles include phospholipids, optionally in admixture with other amphiphilic compounds. Phospholipids are amphiphilic compounds which typically contain at least one phosphate group and at least one, preferably two, lipophilic long-chain hydrocarbon groups.

Examples of suitable phospholipids include esters of glycerol with one or preferably two (equal or different) residues of fatty adds and with phosphoric acid, wherein the phosphoric acid residue is in turn bound to a hydrophilic group, such as, for example, choline (phosphatidylcholines-PC), serine (phosphatidylserines-PS), glycerol (phosphatidylglycerols-PG), ethanolamine (phosphatidylethanolamines-PE), inositol (phosphatidylinositol). Esters of phospholipids with only one residue of fatty acid are generally referred to in the art as the "lyso" forms of the phospholipid or "lysophospholipids".

Fatty acid residues present in the phospholipids are in general long chain aliphatic acids, typically containing from 12 to 24 carbon atoms, preferably from 14 to 22; the aliphatic chain may contain one or more unsaturated portions or is preferably completely saturated. As used herein, the term "phospholipids" includes either naturally occurring, semisynthetic or synthetically prepared products that can be employed either singularly or as mixtures. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic add are employed.

Further examples of phospholipids are phosphatidic acids (e.g. the diesters of glycerol-phosphoric acid with fatty acids); sphingolipids, such as sphingomyelins (e.g. those phosphatidylcholine analogs where the residue of glycerol diester with fatty acids is replaced by a ceramide chain); cardiolipins (e.g. the esters of 1,3-diphosphatidylglycerol with a fatty acid); glycolipids, such as gangliosides GM1 (or GM2) or cerebrosides; glucolipids; sulfatides and glycosphingolipids. Examples of naturally occurring phospholipids include natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acid di-esters of phosphatidylcholine, ethylphosphatidylcholine, phosphatidylglycerol, phosphatidic acid, phosphatidylethanolamine, phosphatidylserine, and sphingomyelin. Examples of preferred phosphorlipids include, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2-Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-steparoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroylphosphatidylglycerol (DLPG) and its alkali metal salts, diarachidoylphosphatidylglycerol (DAPG) and its alkali metal salts, dimyristoylphosphatidylglycerol (DMPG) and its alkali metal salts, dipalmitoylphosphatidyl-glycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoylphosphatidylethanolamine (DMPE), dipalmitoylphospha-tidylethanolamine (DPPE), distearoyl phosphatidylethanolamine (DSPE), dioleylphosphatidyl-ethanolamine (DOPE), diarachidoylphosphatidylethanolamine (DAPE), dilinoleylphosphatidyl-ethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingo-myelin (DS SP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoyl-phosphatidylinositol (DSPI), and dioleoyl-phosphatidylinositol (DOPI).

The term "phospholipid" further includes modified phospholipids, e.g. phospholipids where the hydrophilic group is in turn bound to another hydrophilic group. Examples of modified phospholipids include phosphatidylethanolamines modified with polyethylene glycol (PEG), i.e. phosphatidylethanolamines where the hydrophilic ethanolamine moiety is linked to a PEG molecule of variable molecular weight (e.g. from 300 to 5000 daltons).

Mixtures of phospholipids can also be used, such as, for instance, mixtures of DPPC, DSPC and/or DAPC with DSPS, DPPS, DSPA, DPPA, DSPG, DPPG, Ethyl-DSPC and/or Ethyl-DPPC. Any such combination may further benefit by addition of cholesterol.

The phospholipid is typically the main component of the liposomal envelope or NLC, amounting to at least 50% (w/w) of the total amount of components forming said envelope or NLC. In some preferred embodiments, substantially the totality of the envelope or NLC (i.e. at least 90% and up to 100% by weight) can be formed of phospholipids.

The phospholipids can conveniently be used in admixture with other amphiphilic compounds such as, for instance, fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono-di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol iso-butyrate, cholesterol palmitate, cholesterol stearate, lanosterol acetate, ergosterol palmitate, or phytosterol n-butyrate; sterol esters of sugar acids including cholesterol glucuronides, lanosterol glucoronides, 7-dehydrocholesterol glucoronide, ergosterol glucoronide, cholesterol gluconate, lanosterol gluconate, or ergosterol gluconate; esters of sugar acids and alcohols including lauryl glucoronide, stearoyl glucoronide, myristoyl glucoronide, lauryl gluconate, myristoyl gluconate, or stearoyl gluconate; esters of sugars with aliphatic adds including sucrose laurate, fructose laurate, sucrose palmitate, sucrose stearate, glucuronic acid, gluconic acid or polyuronic acid; trimethylammonium-propane (DOTAP), 1,2-distearoyl-3-dimethylammonium-propane (DSDAP); and mixtures or combinations thereof.

Preferred additional compounds are lipids including cholesterol, ergosterol, phytosterol, sitosterol, lanosterol, tocopherol, propyl gallate or ascorbyl palmitate; fatty acids such as myristic acid, palmitic acid, stearic acid, arachidic acid and salts and derivatives thereof; butylated hydroxytoluene; or mixtures thereof. Particularly preferred is cholesterol. These compounds can be added to the liposome or NLC forming composition in an amount of up to about to 60% by mole of the total composition, preferably up to about 25%.

Optionally, in order to confer a desired overall net charge to the liposome or NLC, the respective envelope includes at least one component bearing an overall net charge, in particular a charged amphiphilic material, preferably a lipid or a phospholipid.

Examples of phospholipids bearing an overall negative charge are derivatives, in particular fatty acid di-ester derivatives, of phosphatidylserine, such as DMPS, DPPS, DSPS; of phosphatidic acid, such as DMPA, DPPA, DSPA; of phosphatidylglycerol such as DMPG, DPPG and DSPG or of phosphatidylinositol, such as DMPI, DPPI or DPPI. Also modified phospholipids, in particular PEG-modified phosphatidylethanolamines, such as DMPE-PEG2000, DMPE-PEG3000, DMPE-PEG4000, DPPE-PEG5000, DPPE-PEG2000, DPPE-PEG3000, DPPE-PEG4000, DPPE-PEG5000, DSPE-PEG2000, DSPE-PEG3000, DSPE-PEG4000, DSPE-PEG5000, DAPE-PEG2000, DAPE-PEG3000, DAPE-PEG4000 or DAPE-PEG5000 can be used as negatively charged molecules. Preferably, the negatively charged compound is selected among DPPA, DPPS, DSPG, DSPE-PEG2000, DSPE-PEG5000 or mixtures thereof.

The negatively charged component is typically associated with a corresponding positive counter-ion, which can be mono- (e.g. an alkali metal or ammonium), di- (e.g. an earth-alkali metal) or tri-valent (e.g. aluminium). Preferably the counter-ion is selected among alkali metal cations, such as $Li^+$, $Na^+$, or $K^+$, more preferably $Na^+$.

Examples of phospholipids bearing an overall positive charge are derivatives of ethylphosphatidylcholine, in particular di-esters of ethylphosphatidylcholine with fatty acids, such as 1,2-Distearoyl-sn-glycero-3-Ethylphosphocholine (Ethyl-DSPC or DSEPC), 1,2-Dipalm-itoyl-sn-glycero-3-Ethylphosphocholine (Ethyl-DPPC or DPEPC). The negative counter-ion is preferably an halogen ion, in particular chlorine or bromine.

In all compositions, a preferred prostaglandin is prostaglandin E2. A preferred antioxidant is α-tocopherol.

Furthermore, the compositions of the present invention can optionally include, in combination with the plurality of lipid nanoparticles, one ore more pharmaceutical excipients selected from humectants, viscosity modifiers, surfactants, pH stabilizers, freeze drying protectants, polymers, and combinations thereof.

Also described herein are methods for treating a pulmonary condition in a mammal by administering to the lungs of a mammal in need thereof a formulation that includes a lipid nanoparticle composition as described herein, wherein the pulmonary condition is selected from pulmonary fibrosis, interstitial lung disease, idiopathic interstitial pneumonia, and asthma. Liposomes remain in the lungs after the inhalation delivery thereby limiting penetration of the payload into the blood stream and accumulation in other organs. Preferably, the formulation is delivered via a nebulizer.

In one embodiment, the lipid nanoparticle composition includes a plurality of lipid nanoparticles, wherein at least one lipid nanoparticle includes: (i) a lipid membrane surrounding an inner compartment of the nanoparticle, (ii) an aqueous phase encapsulated by the inner compartment, and (iii) at least one water-soluble active agent contained within the aqueous phase, wherein the active agent is a water-soluble prostaglandin, wherein each lipid nanoparticle has a diameter ranging from 1 nm to 1000 nm and the lipid nanoparticle further includes 1,2-distearoyl-sn-glycero-3-phosphoethanolamine-N-[amino(polyethylene glycol) bound to an outer lipid surface of the lipid nanoparticle. In another embodiment, the lipid nanoparticle further includes siRNA bound to the lipid nanoparticle via a cationic agent or bound to an outer lipid surface of the lipid nanoparticle via a disulfide bond.

In another embodiment, the lipid nanoparticle composition includes a plurality of lipid nanoparticles, wherein at least one lipid nanoparticle includes: (i) a mixture of solid and liquid lipids and (ii) at least one lipid-soluble active agent contained within the lipid mixture, wherein the active agent is a lipid-soluble prostaglandin, wherein each lipid nanoparticle has a diameter ranging from 1 nm to 1000 nm and the lipid nanoparticle further comprises 1,2-distearoyl-sn-glycero-3-phosphoethanolamine-N-[amino(polyethylene glycol) bound to an outer lipid surface of the lipid nanoparticle. In another embodiment, the lipid nanoparticle further includes siRNA bound to the lipid nanoparticle via a cationic agent or bound to an outer lipid surface of the lipid nanoparticle via a disulfide bond.

The following non-limiting examples serves to further illustrate the present invention.

EXAMPLES

Example 1

Pulmonary Delivery of Prostaglandin E2 (PGE2)

Materials and Methods
Materials

Egg phosphatidylcholine and cholesterol were purchased from Avanti Polar Lipids (Alabaster, Ala.). PGE2 was obtained from Apichem Chemical Technology Co., Ltd. (Shanghai, China), bleomycin was purchased from Sigma Aldrich (Ronkonkoma, N.Y.). Hairless SKH1 mice, 6-8 weeks-old, were purchased from Charles River Laboratories (Wilmington, Mass.).

Liposomal Composition of PGE2

Liposomes were prepared according to the following procedure. Egg phosphotidyl choline and cholesterol were dissolved in 4.0 ml of chloroform at 55:45 ratio (all compounds were obtained from Avanti Polar Lipids, Alabaster, Ala.). The clear lipid solution was evaporated at 25° C. under reduced pressure. A thin layer was formed and rehydrated using 2.0 ml of 0.3 M sodium citrate buffer (pH=4.0).

The lipid mixture was sonicated continuously for 3.0 hours. PGE2-loaded liposomes were prepared from egg phosphatidylcholine and cholesterol (55:45 ratio) using the ethanol instillation method. Dry lipids and PGE2 were dissolved in 98% ethanol at room temperature, 0.9% NaCl has been added to the mixture to reach final lipid and PGE2 concentrations of 20 mM each. The ethanol volume was 10% from final volume.

Obtained liposomes were extruded gradually through 100 nm and 200 nm polycarbonate membranes at room temperature using an extruder device from Northern Lipids, Inc. (Vancouver, BC, Canada). Liposomes were separated from non-encapsulated PGE2 by dialysis against 100 volumes of 0.9% NaCl overnight at 4° C. The encapsulation efficacy of PGE2 in liposomes was ~90-95%. Aliquots of each liposomal formulation were labeled with the near infrared fluorescent dye Cy5.5 Mono NHS Ester (GE Healthcare, Amersham, UK).

The fluorescent dye was dissolved together with lipids in chloroform. Approximate excitation/emission maxima of Cy5.5 were 675 nm/694 nm. Portions of liposomes were labeled with osmium tetroxide (0.5%) that was added to the rehydration buffer. The size of liposomes was measured by dynamic light scattering using a 90 Plus Particle Sizer Analyzer (Brookhaven Instruments Corp., New York, N.Y.). Aliquot of 40 µL of each sample was diluted in 2 mL of saline. Zeta potential was measured on PALS Zeta Potential Analyzer (Brookhaven Instruments Corp, New York, N.Y.). Liposomes were used in a volume of 1.5 mL. All measurements were performed at room temperature. Each parameter was measured in triplicate and average values were calculated. Mean diameter of liposomes was about 500 nm.

Animal Model of IPF and Treatment

Experiments were performed on healthy 6-8 weeks old SKH1-hr hairless mice (20-25 g) obtained from Charles River Laboratories (Wilmington, Mass.). Veterinary care followed the guidelines described in the guide for the care and use of laboratory animals (AAALAC) as well as the requirements established by the animal protocol approved by the Rutgers Institutional Animal Care and Use Committee (IACUC).

All mice were contained in micro-isolated cages under pathogen-free conditions at room temperature with humidity of 40±15% and light/dark cycle on 12 h per day in the animal maintenance facility. Mice were anesthetized via intraperitoneal instillation with 80 mg/kg ketamine and 10-12 mg/kg xylazine (Butler-Schine Animal Health Inc, Dublin, Ohio). Once anesthetized, the mouse was placed on the tilting rodent work stand (Hallowell EMC, Pittsfield, Mass.) in supine position and restrained in position by an incisor loop. The tongue was then extruded via rotation with a cotton tip applicator. The larynx was visualized using a modified 4 mm ear speculum attached to an operating head of an ophthalmoscope (Wellch Allyn, Skaneateles Falls, N.Y.). The modified speculum, acting in an inverted fashion as a laryngoscope blade, provided dorsal displacement of the tongue and magnification of the laryngeal opening as described.

Bleomycin was administered intratracheally in doses of 0.5, 1.0, 1.5, and 2.0 U/kg. Mice were treated with liposomal PGE2 by inhalation twice a week for three weeks starting with the second day after the bleomycin administration. Previously developed instillation unit consisting of a Collison nebulizer connected to four-port, nose-only exposure chambers was used for inhalation delivery of liposomal PEG2. Liposomes were aerosolized at the flow rate of 2 L/min for ten min. Animal weight was measured daily throughout the study. After the three weeks treatment period, all mice were anesthetized with isoflurane and euthanized. The organs (lungs, heart, liver, kidney, spleen, and brain) were excised and used for further analysis.

Gene Expression

Mouse lungs were extracted, trachea and mainstream bronchi were separated, lungs were frozen and homogenized. RNA was isolated using an RNeasy kit (Qiagen, Valencia, Calif.) according to manufacturer's protocol. First-strand cDNA was synthesized with Ready-To-Go You-Prime First-Strand Beads (Amersham Biosciences, Piscataway, N.J.) with 1 µg of total cellular RNA (from $10^7$ cells) and 100 ng of random hexadeoxynucleotide primer (Amersham Biosciences, Piscataway, N.J.). After synthesis, the reaction mixture was immediately subjected to quantitative polymerase chain reaction (QPCR). A standard Mouse Fibrosis RT Profiler™ PCR Array panel from SABiosciences (Quiagen, Valencia, Calif.) was used.

The assay was performed on lung samples from healthy mice (control), mice with lung fibrosis and mice with lung fibrosis treated with liposomal PGE2. QPCR was performed using SYBER Green Master Mix as detection agent. Fold change of the gene expression was measured using SABioscience internet software which compares the expression of tested genes with that of housekeeping genes and expresses fold change in gene expression as $\Delta\Delta Ct$ values ($\Delta\Delta Ct=\Delta Ct_{treated}-\Delta Ct_{control}$). PCR specificity was verified by melting curve and gel electrophoresis. In addition to the panel of genes provided in mouse fibrosis array, the expression of genes encoding Hypoxia Inducible Factor 1α (HIF1A), von Hippel-Lindau (VHL) and β-actin (B-ACTIN, internal standard) was measured as previously described.

Histopathologic Analysis

At the end of the experiments, the animals were euthanized, the lungs were extracted and immediately fixed in 10% phosphate-buffered formalin. Samples were subsequently dehydrated and embedded in Paraplast®. Five-micrometer sections were cut and stained with hematoxylin-eosin as previously described and analyzed.

Immunohistochemistry

To visualize the expression of proteins, immunohistochemical staining was conducted on paraffin-embedded slides of pulmonary tissue. Slides (5 µm) were deparaffiized in xylene for 5 min followed by progressive rehydration in 100%, 95%, 70%, and 50% ethanol for 3 min during each step. Endogenous peroxidase activity was blocked by incubating slides in 3% $H_2O_2$ solution in methanol at room temperature for 10 min and washing in 300 mL PBS two times for 5 min.

The slides were then stained with anti-mouse monoclonal antibodies for VEGF, CCL12, MMP3 and HIF1A proteins. Antibodies against VEGF (labeled with Alexa Fluor 488 fluorescence dye) and MMP3 (labeled with FITC) were obtained from Biolegend, San Diego, Calif. Antibodies against CCL12 and HIF1A (both labeled with FITC) were purchased from Biorbyt, Cambridge, UK and from Novus Biologicals, Littleton, Colo., respectively. All antibodies were used in in the dilution of 1:100. The slides were stained using Vector M.O.M. Immunodetection Kit (Vector Lab., Inc., Burlingame, Calif.), visualized and photographed using a fluorescence microscope (Olympus IX71, Center Valley, Pa.).

Hydroxyproline Assay

Fourteen days after bleomycin instillation, lungs were harvested, homogenized in distilled water and examined using a Biovision hydroxyproline assay kit (Biovision, Mount View, Calif.). Homogenized lung tissues were hydrolyzed in 12 N HCl at 120° C. for 3 h in pressure-tight vials. After this, 10 µl of samples were allocated to a 96 well plate and dried under vacuum. Oxidation buffer with chloramine T was added to each sample at room temperature for 5 min, and the samples were incubated in dimethylaminobenzaldehyde (DMAB) reagent for 90 min at 60° C. Samples were cooled and the absorbance at 560 nm was measured using an automated microplate reader. Six concentrations of hydroxyproline standard dilutions (from 0 to 1 µg/well) were used to plot a hydroxyproline standard curve.

Content of Liposomes in Different Organs

The distribution of fluorescent-labeled liposomes was examined in mouse lungs, heart, liver, spleen, kidneys, and brain. The organs were excised, rinsed in saline, and fluorescence was registered by IVIS imaging system (Xenogen Corporation, Alameda, Calif.). Visible light and fluorescence images were taken and overlaid. The intensity of fluorescence was represented on composite light/fluorescent images by different colors, with blue reflecting the lowest fluorescence intensity and red—the highest intensity. Images of each organ were then scanned and total fluorescence intensity was calculated as previously described.

Preliminary experiments showed a strong linear correlation between the total amount of labeled substance accumulated in the organ and calculated total fluorescence intensity. The fluorescence was expressed in arbitrary units with 1 units represented approximately $2 \times 10^{10}$ photons/s/sr/cm$^2$. The method allows a quantitative comparison of the concentration of the same fluorescent dye between different series of the experiments. The mass of all organs was measured. The fluorescence intensity was normalized for organ weight.

Internalization of Liposomes by Lung Cells

Internalization of osmium-labeled liposomes by lung cells was studied by electron transmission microscopy in lung tissue sections fixed prior to microscopy using standard techniques as previously described. Briefly, lung tissue slices were fixed for 2 hours in Trump's EM Fixative (combination of low concentration of both formaldehyde and glutaraldehyde in 0.1 M Milloning's Phosphate buffer, pH 7.3). Post fixation was carried out in 1% osmium tetroxide in buffer for 1 hour followed by dehydration in graded ethanol series and embedment in Spurr's Low Viscosity Resin. Sections were prepared using a diamond knife on a LKB-2088 Ultramicrotome (LKB-Produkter/Bromma, Sweden). Observation and micrographs were made with a JEM-100CXII Electron Microscope (JEOL Ltd., Tokyo, Japan).

Statistical Analysis

Data were analyzed using descriptive statistics and single-factor ANOVA, and are presented as a mean±SD from five independent measurements. Five to ten animals were used in each experimental group. The analyzed data sets for significance with Student's t test and considered P values of less than 0.05 as statistically significant.

Results

Selection of Bleomycin Dose

In order to select an appropriate dose of bleomycin, four doses (0.5; 1.0; 1.5; 2.0 U/kg) were tested. Bleomycin was instilled intratracheally and mice were observed for 21 days after the instillation. The dose of 2.0 U/kg led to the death of 100% of animals within 21 days (FIG. 1A). The doses of 1.5 and 1.0 U/kg induced death of 50 and 25% of animals, respectively. The lowest tested dose (0.5 U/kg) did not induce animal death. Based on these results, 1.5 U/kg dose of bleomycin was selected for the main experiments (FIGS. 1A and B).

Validation of IPF Model

Figure 2:
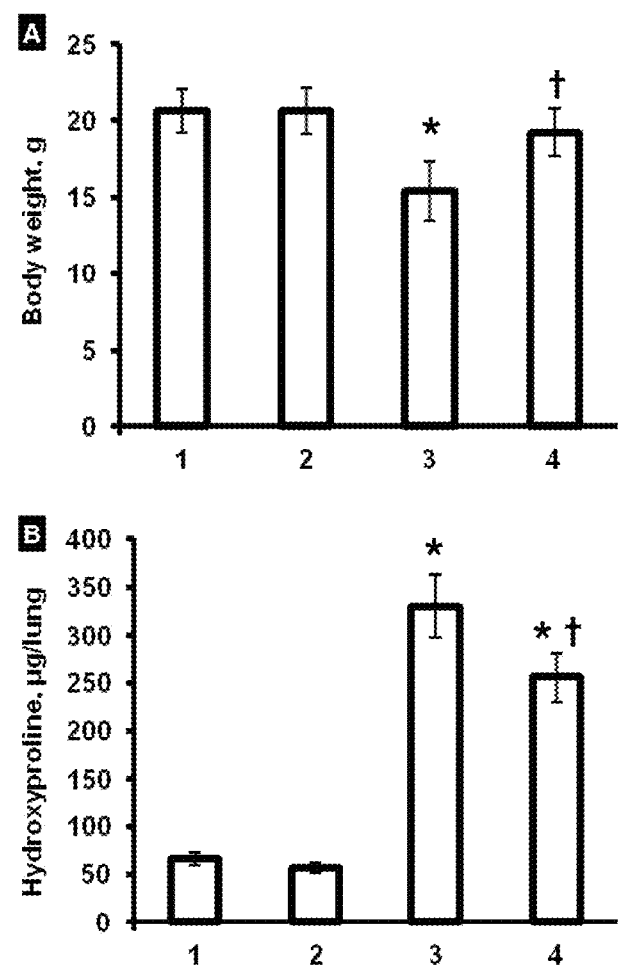
FIGS. 2A-B show the influence of inhalation treatment with liposomal PGE2 on body mass (A) and hydroxyproline content in the lungs (B) (1—Healthy mice (control); 2—Mice instilled with bleomycin (1.5 U/kg); 3—Mice instilled with bleomycin (1.5 U/kg) and treated by inhalation with liposomal PGE2)
Figure 3:
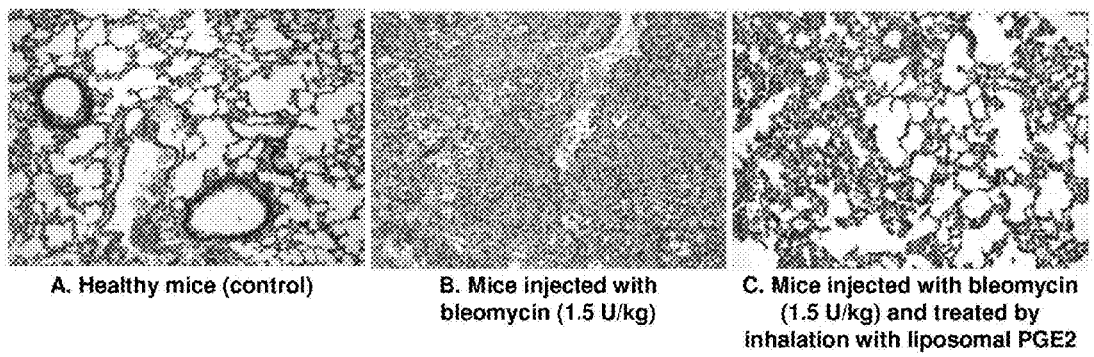
FIGS. 3A-C depict lung histology ((A) Healthy mice (control); (B) Lung fibrosis was induced by intratracheal instillation of 1.5 U/kg of bleomycin; (C) Mice were treated with inhalation of liposomal PGE2 within 3 weeks twice a week starting one day after the bleomycin administration)

Changes in animal body mass, hydroxyproline content in the lung tissue and lung histology were used as hallmarks of the development of IPF in experimental animals after the instillation of 1.5 U/kg bleomycin. It was found that three weeks after the instillation, the body mass of animals decreased to 75% (P<0.05) of its initial value (FIG. 2A). At the same experimental point, the concentration of hydroxyproline in the lungs increased in 2.6 times (FIG. 2B). Histological analysis of control lung tissue demonstrated widely patent alveoli without inflammation or edema (FIG. 3A). The bronchi were also patent. Lungs of animals instilled with bleomycin (FIG. 3B) showed consolidation of the pulmonary architecture, with early fibrotic thickening of the alveolar walls, ablation of the alveolar space, and edema. Chronic inflammatory cells and fibroblasts were readily apparent within the affected areas. Taken together, these data clearly confirm the development of marked lung fibrosis in experimental animals subjected to bleomycin.

Body Distribution and Accumulation of Liposomes in the Lungs

Figure 4:
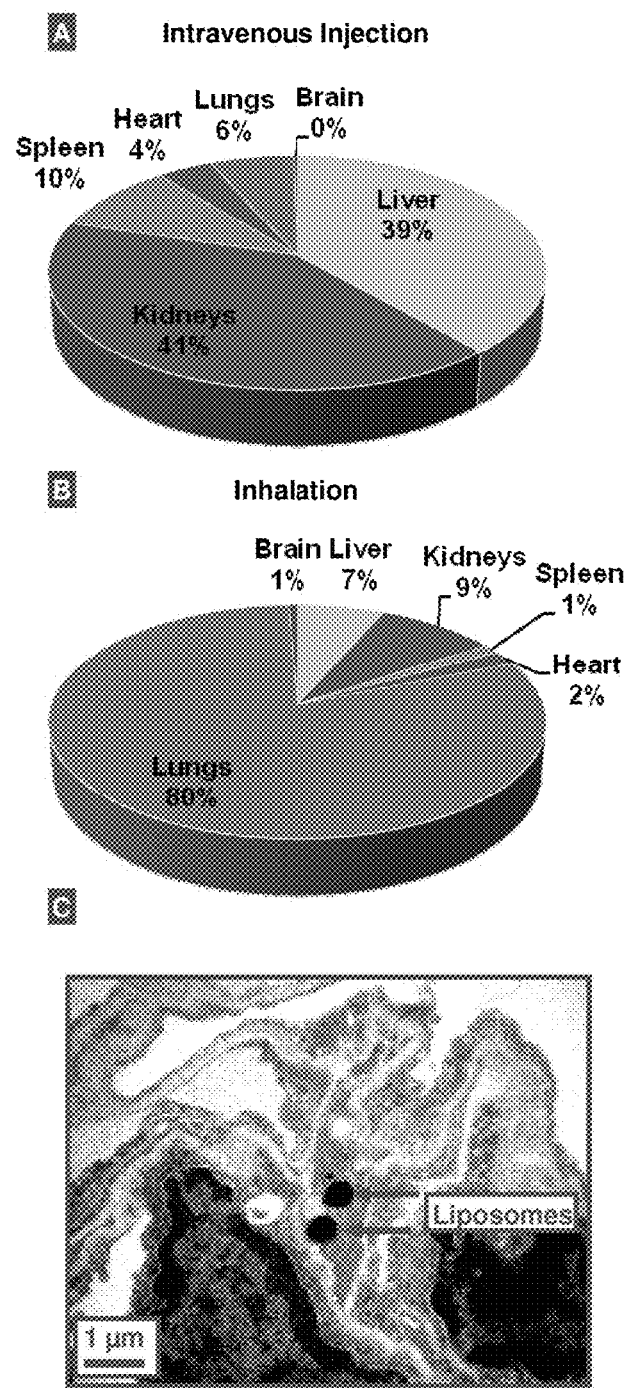
FIGS. 4A-B depict tissue content of liposomes (relative tissue content of liposomes delivered to mice by intravenous instillation (A) or inhalation (B); (C) localization of liposomes in the mouse lung tissues after the inhalation delivery)

The average size of liposomes used in the present study for inhalation was 500-600 nm. Liposomes remain predominately in the lungs for a long period of time after inhalation. In order to confirm the preferential pulmonary accumulation of used in the present study liposomes, the present inventors studied organ content of fluorescently-labeled liposomes using the IVIS imaging system (FIG. 4).

Inhalation delivery was compared with intravenous instillation of similar liposomes. It was found that 24 hours after intravenous instillation, liposomes accumulated predominately in the kidneys and liver, while substantially lesser accumulation was found in the spleen, heart and lungs. Only trace amount of liposomes registered in the brain. In contrast, after inhalation delivery, liposomes were retained in the lungs with minimal amounts found in other organs including the liver, kidneys, spleen, heart and brain. These data confirmed the favorable distribution of inhaled liposomes and formed the basis for the use of such liposomes as carriers to deliver PGE2 locally to the lungs and limitation of possible adverse systemic effects of PGE2. In order to study the penetration of liposomes into lung cells after inhalation, lipid membrane of liposomes was labeled by osmium tetroxide and visualized in lung tissues by transmission electron microscopy (FIG. 4C). These data clearly showed that liposomes did penetrated lung cells after inhalation and accumulated in the cytoplasm.

Treatment of IPF with Liposomal Form of PGE2

In order to estimate anti-fibrotic effect of liposomal PGE2, we investigated the influence of this preparation on body mass, hydroxyproline content in the lungs and mortality of animals with IPF, induced by a single intratracheal instillation of bleomycin. Treatment with liposomal PGE2 prevented the decrease in the body mass of experimental animals induced by bleomycin (FIG. 2A). The difference between body mass in bleomycin-treated animals with IPF (FIG. 2A, bar 2) and animals instilled with bleomycin and treated with liposomal PGE2 (FIG. 2A, bar 3) was statistically significant (P<0.05). A therapeutic action of liposomal PGE2 was also confirmed by the measurement of hydroxyproline content in the lungs.

It was found that treatment of bleomycin-treated animals with liposomal PGE2 significantly decreased (P<0.05) the accumulation of hydroxyproline in lung tissues by 1.3 fold (FIG. 2B). However, the content of hydroxyproline in the lung tissues still was significantly (P <0.05) higher (~2 times) when compared with bleomycin positive control (compare bars 3 and 1 in FIG. 2B). Inhalation treatment of animals with liposomal PGE2 substantially limited lung tissue damage induced by bleomycin (FIG. 3C). Some mild thickening of the alveolar septa was noted focally, and in some areas fibrosis could still be observed. However, both the extent and severity of the fibrotic process were reduced in this group. Edema was minimal and only focal inflammation was present. Finally, inhalation treatment of animals with pulmonary fibrosis by liposomal PGE2 completely prevented the mortality of experimental animals (FIG. 1B).

Gene and Protein Expression

Figure 5:
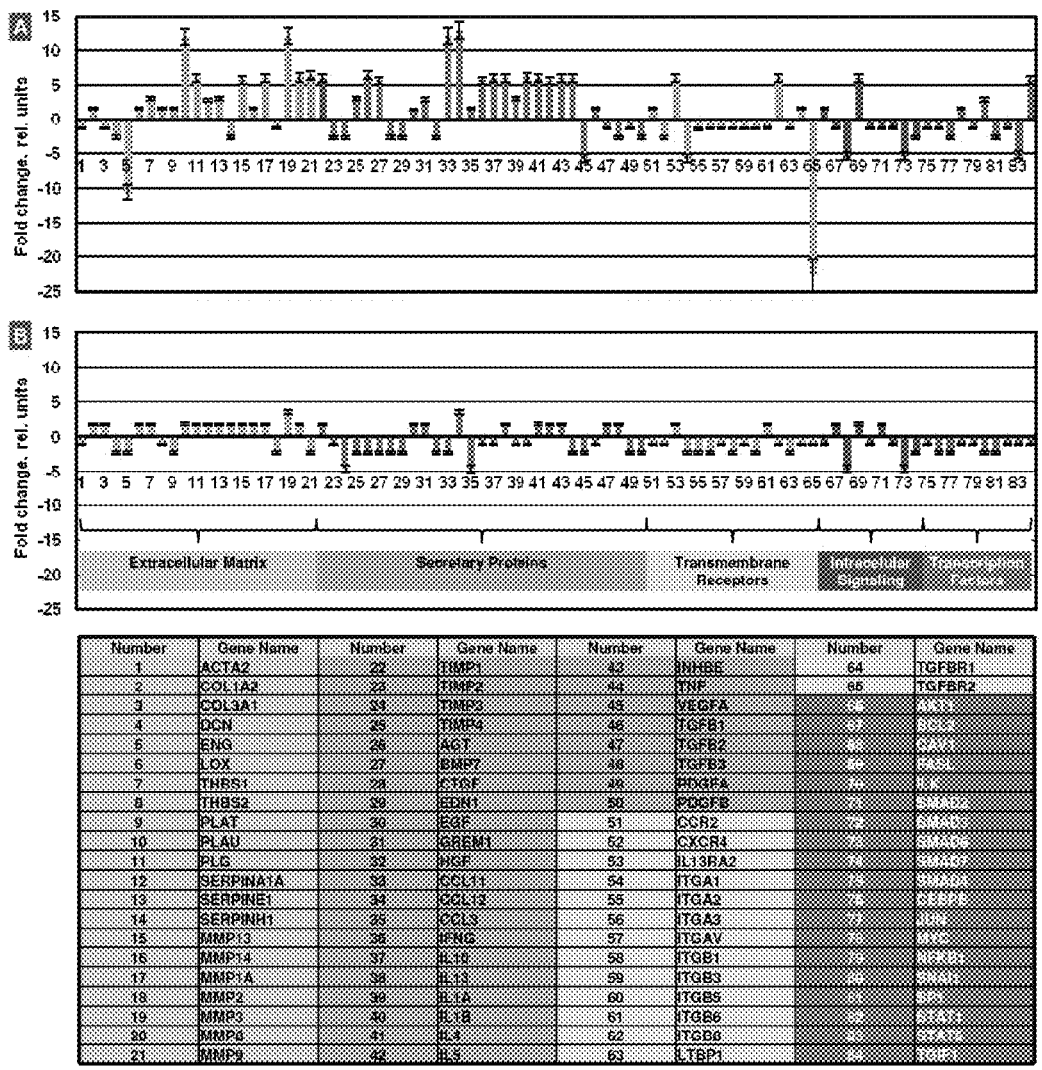
FIGS. 5A-B depict gene expression measured by the Quantitative Polymerase Chain Reaction (QPCR) ((A) Mice instilled with bleomycin (1.5 U/kg); (B) Mice instilled with bleomycin (1.5 U/kg) and treated by inhalation with liposomal PGE2)

In order to examine mechanisms of the development of fibrosis induced by intratracheal instillation of bleomycin and protective effect of liposomal PGE2 delivered to the lungs by inhalation, we studied the profiles of the expression of 84 key genes involved in tissue remodeling during wound repair and development of fibrosis. The data obtained using the standard Mouse Fibrosis RT Profiler™ PCR Array panel showed that after instillation of bleomycin, 24 studied genes were upregulated by more than 5 times while 7 out of 84 genes were downregulated more than 5-fold (FIG. 5A).

Data showed that transforming growth factor (TGF)-mediated cell signaling was impaired in mice after the instillation of bleomycin. While the expression of genes encoding different types of TGF proteins was practically unaffected, the expression of proteins associated with TGF receptors and their second messenger (ENG, TGFBR2 and SMAD6 genes, FIG. 5A, #5, 65, and 73, respectively) was significantly downregulated. In addition to TGF signaling, the expression of genes encoding vascular endothelial growth factor (VEGF), integrin alpha-1 (ITGA1), calveolae protein (CAV1) signal transducer and activator of transcription 6 (STATE) were also decreased (FIG. 5A, #45, 54, 68, and 83, respectively).

Figure 6:
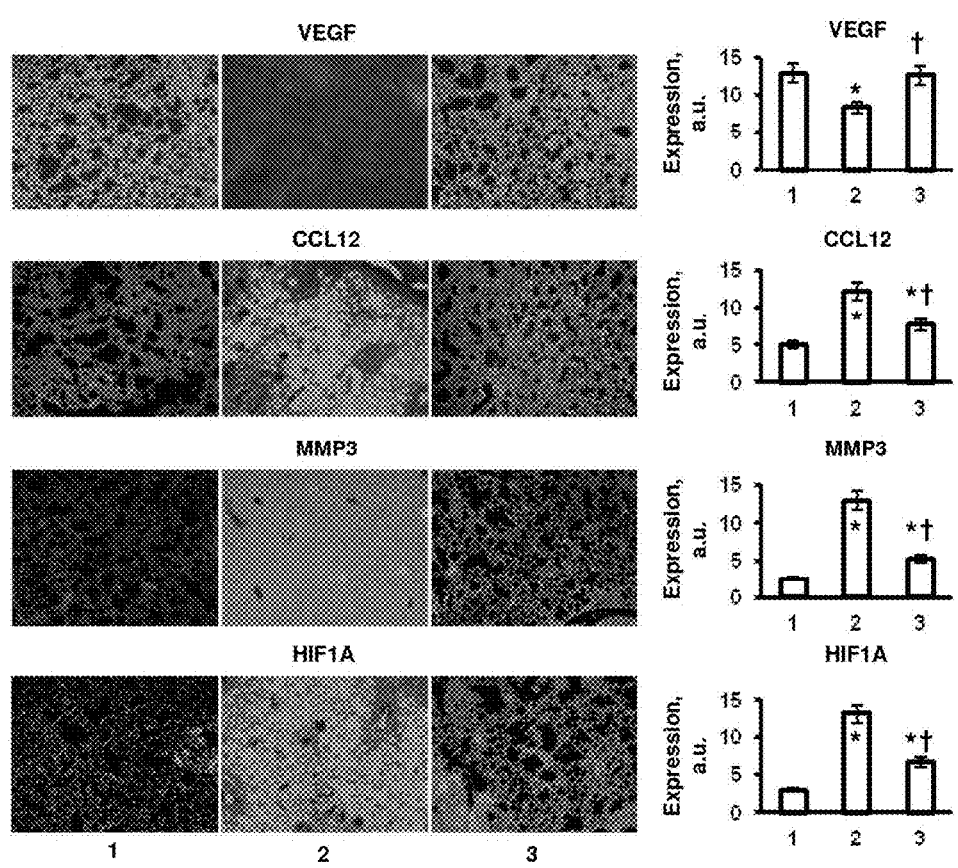
FIG. 6 provides representative images of tissue sections stained with antibodies against VEGF, CCL12, MMP3 and HIF1A proteins (10× magnification) ((1) Healthy mice (control); (2) Mice instilled with bleomycin (1.5 U/kg); (3) Mice instilled with bleomycin (1.5 U/kg) and treated by inhalation with liposomal PGE2)

In order to confirm data obtained by the QPCR, the expression of VEGF protein was also examined in lung tissues using immunostaining of tissue sections (FIG. 6). The data obtained confirmed QPCR results and showed that VEGF protein expression was substantially decreased after instillation of bleomycin. In contrast, the expression of genes encoding the following functional groups of proteins was substantially increased after bleomycin instillation: plasminogen and plasminogen activator (PLG and PLAU, FIG. 5A, #10 and 11), several matrix metalloproteinases (MMP13, MMP1A, MMP3, MMP8, and MMP9, FIG. 5A, #15, 17, 19, 20, and 21) as well as tissue inhibitor of metalloproteinases (TIMP1—FIG. 5A, #22), angiotensinogen and a member of the TGF-beta family (AGT and BMP7, FIG. 5A, #26 and 27), chemokines (CCL11 and CCL12, FIG. 5A. #33 and 34), gamma interferon (IFNG, FIG. 4A, #36), several interleukins (IL10, IL13, IL1B, 1L4, and IL5, FIG. 5A, #37, 38, 40, 41, and 24, respectively) and interleukin 13 receptor (IL13RA2, FIG. 5A, #53), inhibin (INHBE, FIG. 5A, #43), tumor necrosis factor and its ligand (TNF and FASL, FIG. 5A, #44 and 69), integrin (ITGB8, FIG. 5A, #62) and transforming growth factor-beta-induced factor (TGIF1, FIG. 5A, #84).

Figure 7:
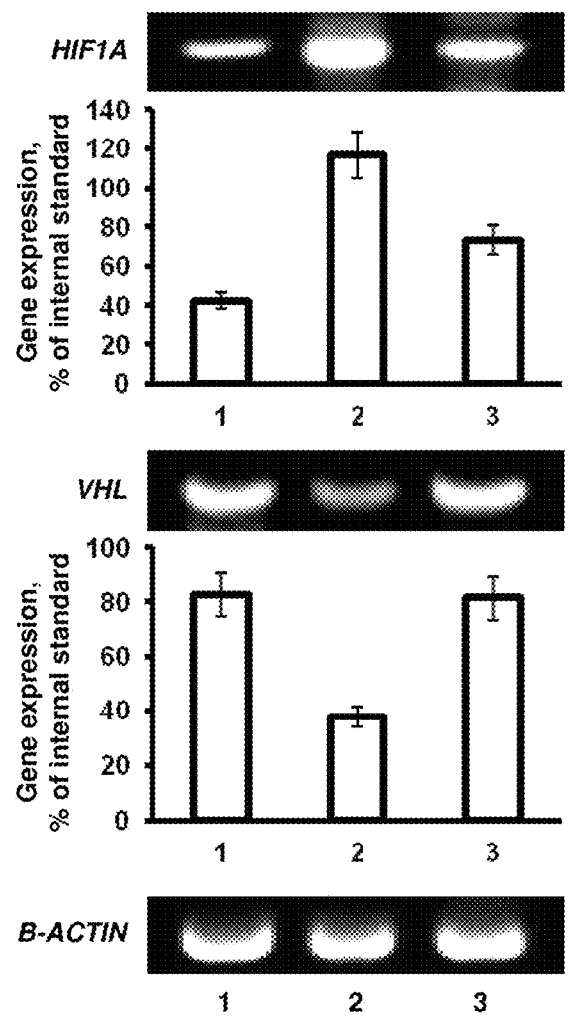
FIG. 7 provides representative images of gel electrophoresis of RT-PCR product of genes encoding hypoxia inducible factor 1α (HIF1A), von Hippel-Lindau (VHL) and β-actin (B-ACTIN, internal standard) proteins.

Immunohistochemical measurement of the expression of chemokine CCL12 and matrix metalloproteinase MMP3 confirmed that bleomycin instillation induced overexpression of both proteins. In addition to genes included in the mouse fibrosis array, the expression of hypoxia inducible factor 1 alpha (HIF1A) and von Hippel-Lindau (VHL) genes and proteins were analyzed by RT-PCR and immunohistochemical staining, respectively. It was found that instillation of bleomycin led to the overexpression of HIF1A and suppression of VHL genes (FIG. 7). Analysis of the expression of HIF1A protein supports RT-PCR finding and show that the expression of this protein was also upregulated after bleomycin instillation (FIG. 6). Notably, that treatment of mice with liposomal PGE2 delivered by inhalation after instillation of bleomycin almost completely eliminated the aforementioned disturbances in gene and protein expression (FIGS. 5B, 6 and 7).

Discussion

The present invention shows that intratracheal instillation of bleomycin in dose of 1.5 U/kg induces extensive lung fibrosis. Subsequently, development of fibrosis was initiated by a marked pulmonary inflammation with subsequent transition into fibrosis. The sequence of the process was confirmed by morphological features of inflammation and overexpression of several genes involved in the development of inflammation.

In fact, several chemokines, inflammatory cytokines and interleukins were overexpressed following bleomycin treatment. chemokines role is important in the pulmonary recruitment of granulocytes and are essential in the pathogenesis of bleomycin-induced lung fibrosis. Moreover, interferon-gamma, an inflammatory cytokine, was implicated in the development of fibrosis in inflamed tissues. The gene encoding this protein was also overexpressed after instillation of bleomycin. In addition, all analyzed genes encoding interleukins were overexpressed in the lungs after bleomycin treatment.

It is well known that interleukins are important mediators of inflammation and remodeling in the lungs. In particular, it was found that the overexpression of interleukin IL10 in the lung causes mucosal metaplasia, tissue inflammation, subepithelial fibrosis and airway remodeling via IL13-dependent and -independent pathways. IL13-depended pathway was definitely involved in the development of fibrosis after inflammation in the present study. The registered overexpression of the IL13 gene as well as gene encoding IL3 receptors (IL13RA2) supports this suggestion. Interleukin 13 is considered to be a major inducer of fibrosis in several different disease conditions.

The activation of inflammation and its transition to fibrosis was associated with the overexpression of several matrix metalloproteinases (collagenases/gelatinases). It is possible that such activation was compensatory and directed to the degrading of fibrillar collagens in order to limit their accumulation during pulmonary fibrosis. However, the activation of these enzymes might also enhance tissue damage during IPF. Therefore, the present experimental data support the hypothesis that pulmonary fibrosis is preceded by a chronic inflammatory process which induces lung injury, modulates fibrogenesis, provokes fibrosis and leads to the formation of the fibrotic scar. It is generally assumed that the transforming growth factor-beta (TGFB) family of receptors may play an important role in the initiation of the signal transduction that leads to mitogenic responses and initiation of fibrosis by induced myofibroblast differentiation. However, experimental data suggest that this signal transduction pathway probably did not have a significant impact on the development of pulmonary fibrosis in the present study because genes encoding proteins and receptors involved in this pathways were either practically unchanged or downregulated after the instillation of bleomycin.

Only TGIF1 and bone morphogenetic protein-7 is (a member of the TGFB superfamily) were substantially upregulated in these conditions, suggesting that other than TGFB receptor-initiated signaling pathways might be involved in the development of fibrosis. A second important mediator of inflammation and fibrosis, tumor necrosis factor (TNF), a multifunctional proinflammatory cytokine secreted predominantly by monocytes/macrophages, was upregulated along with tumor necrosis factor ligand superfamily member 6 (encoding by the FASL or TNFSF6 gene) after instillation of bleomycin. These proteins are known to mediate the transition from pulmonary inflammation to fibrosis as well as to induce apoptosis.

Several other signal transduction pathways activated in the lung after instillation of bleomycin, including inhibins, angiotensinogens and integrins, might also be involved in the development of pulmonary fibrosis and tissue damage in the present experimental model.

It is generally believed that fibrosis is accompanied by hypoxia and major hypoxic signaling pathways initiated by HIF1A and VHL proteins contribute in the development and compensation of fibrotic damage. In many cases, it was found that tissue hypoxia promotes fibrosis and HIFA-associated signaling pathways of hypoxia are involved on the development to fibrosis in the liver and lungs.

The present inventors found that instillation of bleomycin induces overexpression of HIF1A gene and protein and inhibits the expression of its counterpart—the VHL gene. This supports the role of HIF1A signaling pathways in the development of lung fibrosis after bleomycin instillation. It was discovered that, independently of HIF1A, pVHL protein encoded by the VHL gene might be directly involved in the development of IPF.

However, it is unlikely that this mechanism was involved in the present study because the VHL gene was suppressed in lung tissues following instillation of bleomycin. It was also found that the overexpression of HIF1A protein can promote the development of IPF via TGF-beta-signaling pathways. However, it is unlikely that such a pathway was involved in the present study because, as noted above, genes encoding proteins and receptors involved in this pathway were either unchanged or downregulated after the instillation of bleomycin.

The present experimental work demonstrates, for the first time, that treatment of pulmonary fibrosis by liposomal PGE2 delivered by inhalation results in remarkably increased survival, limitation of all studied symptoms of IPF developed after intratracheal instillation of bleomycin. The data show that liposomal PGE2 delivered locally to the lungs eliminated the decrease in the mouse body mass, substantially limited hydroxyproline content in the lungs, disturbances in the mRNA and protein expression, restricted lung tissue damage and completely prevented animal mortality.

Example 2

Pulmonary Delivery of PGE2 and siRNA with Nanostructured Lipid Carriers

Materials and Methods
Materials

The nanocarrier-based drug delivery system (DDS) contained: a neutral nanostructured lipid carrier (NLC), PGE2, and thiol-modified siRNA as a suppressor of targeted mRNA. (FIG. 8A). The DDS was coated with poly(ethylene glycol) (PEG). Lipophilic PGE2 was incorporated inside the lipophilic inner core of the NLC. Drug loaded NLC was prepared by a modified melted ultrasonic dispersion method. PGE2 dissolved in 1 mL of DMSO was added to the hot lipid phase consisting of 100 mg Precirol ATO 5 (solid lipid), 100 mg Squalene (liquid lipid) and 5 mg SPC (lipophilic emulsifier). An aqueous phase was prepared by dissolving 250 mg Tween-80 (surfactant) in 10 mL of water. In order to prepare PEG coated NLC, 10 mg DSPE-PEG-COOH (or DSPE-PEG-LHRH for targeted NLC) was added to the aqueous phase. To covalently attach siRNA, thiol modified siRNA was added to the lipid phase. Both phases were maintained for 15 min at 60° C. in the oil bath under magnetic stifling. Then the hot lipid phase was added slowly to the aqueous solution and dispersed using a high-speed homogenizer (PRO Scientific Inc. Oxford, Conn.) for 5 min at 12,000 RPM. The crude emulsion was additionally treated by a probe type ultrasonicator (Model 120 Sonic Dismembrator, Fisher Scientific, Fairlawn, N.J.) for 5 min at 3 W. Then the hot emulsion was cooled to 4° C. in an ice bath, maintaining the mechanical stifling for 60 min. After preparation, the NLC was purified by dialysis (MWC 10,000) and subjected to lyophilization. Mannitol (5%) was added into NLC suspension as a cryoprotector. The obtained powder was stored at 4° C. until further use.

Some of the nanoparticles and/or their payloads were labeled with a fluorescent dye (Cy5.5 or Green 6-FAM) in order to analyze their intracellular accumulation and/or organ distribution. Cy5.5 labeled NLC were prepared by adding DSPE-PEG-COOH:DSPE-PEG-Cy5.5 (10:1) to the hot lipid phase instead of DSPE-PEG-COOH. siRNA labeled with Green 6-FAM was purchased from Dharmacon, Inc. (Chicago, Ill.). The synthesized nanocarriers and DDS were characterized by several different methods including atomic force microscopy, HPLC, MALDI/TOF spectrometry, Zeta potential and molecular modeling in order to confirm the composition, molecular mass and structure of the DDS. Stability of DDS during storage as well as its cellular internalization, localization and release profile of active components was studied in vitro using saline, serum and human fibroblast culture. Similarly, changes in particle size, shape, the stability and functionality of siRNA after nebulization were studied using dynamic light scattering, atomic force microscope, EtBr replacement assay and quantitative RT-PCR. Cytotoxicity and genotoxicity of DDS were studied in vitro.

Animal Model of IPF and Treatment

Healthy 6-8 weeks old SKH1-hr hairless mice of both genders (20-25 g) were obtained from Charles River Laboratories (Wilmington, Mass.). IPF was initiated by the intratracheal instillation of bleomycin at the dose of 1.5 U/kg. Changes in animal body and lung weight, hydroxyproline content in the lung tissue, and lung histology were used as hallmarks of the development of IPF in experimental animals.

Mice were treated separately with three different NLC-based DDS containing PGE2 and siRNA targeted to MMP3, CCL12 and HIF1A mRNA with appropriate controls by inhalation twice a week for three weeks starting 15 days after the bleomycin administration. The development of IPF on day 15 after intratracheal administration of bleomycin was supported by the decrease in body weight, increase in lung weight and hydroxyproline in the lung tissues, magnetic resonance imaging and morphological changes in the lungs. (FIG. 8 B-E). A previously developed installation unit consisting of a collision nebulizer connected to four-port, nose-only exposure chambers was used for inhalation delivery of NLC-PEG2-siRNA. NLC-based DDS was aerosolized at the flow rate of 2 L/min for ten min. Animal weight was measured daily throughout the study. In vivo imaging was performed twice per week in anesthetized mice during the whole course of the treatment. Optical Imaging (In-Vivo MS FX PRO, IVIS 100) and ultrasound (Vevo 2100 imaging system) was performed to monitor the body distribution of nanoparticles and disease progression, respectively. Animals were treated 6 times (2 times per week) starting from the day 15 after bleomycin instillation.

Gene Expression

Expression of genes and proteins involved in the development and compensation of IPF was studied by quantitative RT-PCR (genes), Western blotting and Immunohistochemistry (proteins). In addition, body and organ weights as well as hydroxyproline content in the lungs was monitored. The distribution of osmium-, fluorescent- or tritium-labeled DDS was examined in mouse lungs, heart, liver, spleen, kidneys, and brain using transmission electron and confocal microscopes, optical imaging systems, and a radioactive counter, respectively. Adverse side effects of the treatment were determined by histopathological analysis, apoptosis and necrosis measurement in the healthy organs (heart, liver, spleen, kidneys, and brain).

Histopathologic Analysis

Changes in animal body and lung weight, hydroxyproline content in the lung tissue and lung histology were used as hallmarks of the development of IPF in experimental animals after the instillation of 1.5 U/kg of bleomycin. 15 days after the instillation, the body weight of animals decreased to 75% ($P<0.05$) of its initial value (FIG. 9A) while the lung weight significantly increased (FIG. 9B). At the same experimental point, the concentration of hydroxyproline (one of the major criteria of IPF) in the lungs increased by 2.6 fold (FIG. 9C). Fibrotic changes in the lungs were also documented by MRI imaging of live anesthetized animals (FIG. 9D). Lungs of animals instilled with bleomycin (FIG. 9F) showed consolidation of the pulmonary architecture, with early fibrotic thickening of the alveolar walls, ablation of the alveolar space, and edema. Chronic inflammatory cells and fibroblasts were readily apparent within the affected areas. Taken together, these data clearly confirm the development of marked lung fibrosis in experimental animals subjected to bleomycin.

Changes in size and shape of nanoparticles were analyzed before and after nebulization using dynamic light scattering and atomic force microscope, respectively. Data obtained showed that nebulization in optimized regimen did not influence significantly the characteristics of DDS (FIGS. 8B and C).

Effects of Nebulization on Stability

To further examine how nebulization of nanoparticles influence the stability and functionality of delivered siRNA, the stability of siRNA in serum and its specific activity in terms of the silencing of targeted mRNA were studied using EtBr replacement assay and quantitative RT-PCR, respectively. Naked siRNA almost completely degraded in serum within 5-15 min of incubation (FIG. 8D, upper panel). In contrast, siRNA conjugated to NLC carrier was stable for at least 48 h (FIG. 8D, middle panel). Nebulization did not influence the stability of the nanoparticles and conjugated siRNA (FIG. 8D, bottom panel). In contrast to naked siRNA, siRNA conjugated to NLC effectively suppressed targeted mRNA. It should be stressed that nebulization did not influence functionality and silencing effect of siRNA (FIG. 8E).

Content of NLCs in Different Organs

Organ content of fluorescently-labeled NLC and liposomes after intravenous or intratracheal delivery was examined using the optical imaging system (FIG. 10). Inhalation delivery was accomplished by a special 5-port animal nose-only exposure system. 24 hours after intravenous instillation, NLC and liposomes accumulated predominately in the liver, kidneys and spleen, while substantially lesser accumulation was found in the heart and lungs (FIG. 10). In contrast, after inhalation delivery, NLC and liposomes were retained in the lungs with minimal amounts found in other organs, including the liver. These data confirmed that the NLC can effectively deliver PGE2 and siRNA by inhalation locally to the lungs and limit possible adverse systemic effects of the treatment.

Two types of experiments were carried out to study the cellular internalization of NLC. In the first series, NLC were labeled with osmium tetroxide and delivered to the mice by inhalation. Lungs were excised 24 h after the inhalation and samples cut using an ultramicrotome. Transmission electron microscope (TEM) images of lung tissue sections clearly showed that NLC penetrated lung cells after inhalation (FIG. 11A). To further investigate intracellular localization of siRNA delivered by NLC, siRNA was labeled by a fluorescence dye, incubated cells with naked siRNA and NLC-siRNA nanoparticles and visualized siRNA by confocal microscopy (FIGS. 11B-C). The cell nuclei were stained with DAPI dye (FIG. 11C). siRNA delivered by NLC was internalized by the cells and accumulated predominately in the cytoplasm (FIG. 11D). In contrast, naked siRNA practically did not penetrate the plasma membrane and only a trace amount of fluorescently labeled siRNA was registered in the cytoplasm (FIG. 11B).

Anti-Fibrotic Effect of PGE2

In order to estimate the anti-fibrotic effect of PGE2, the influence of this drug delivered by liposomes or NLC on animal survival, body weight, hydroxyproline content in the lungs of untreated and treated mice with IPF induced by a single intratracheal instillation of bleomycin was studied. The treatment started at day 15 after bleomycin instillation where IPF fully developed. Empty liposomes or NLC delivered alone by inhalation did not significantly influence any studied parameters (FIGS. 9A-C). The treatment with PGE2 delivered by inhalation decreased the body weight of experimental animals induced by bleomycin (FIG. 9A) but had a little effect on the lung weight (FIG. 9B). Therapeutic action of PGE2 was also confirmed by the measurement of hydroxyproline content in the lungs (FIG. 9C).

However, hydroxyproline content in the lungs of treated animals was still significantly higher when compared with healthy untreated control animals (FIG. 9C). Inhalation treatment of animals with liposomal PGE2 substantially limited lung tissue damage induced by bleomycin (FIGS. 9D and E). However, a detectable level of lung fibrotic injury was still registered by MRI in the lungs after the treatment (FIG. 9D). Some mild thickening of the alveolar septa was noted focally, and in some areas mild fibrosis, inflammation, edema and hypoxia features were still observed (FIG. 9E). Therapeutic effects of PGE2 delivered by liposomes and NLC were comparable. Although a substantial correction of IPF was accomplished by inhalation with PGE2 alone, several signs of the disease were still preserved and complete prevention of IPF was not achieved.

Gene and Protein Expression

Figure 12A:
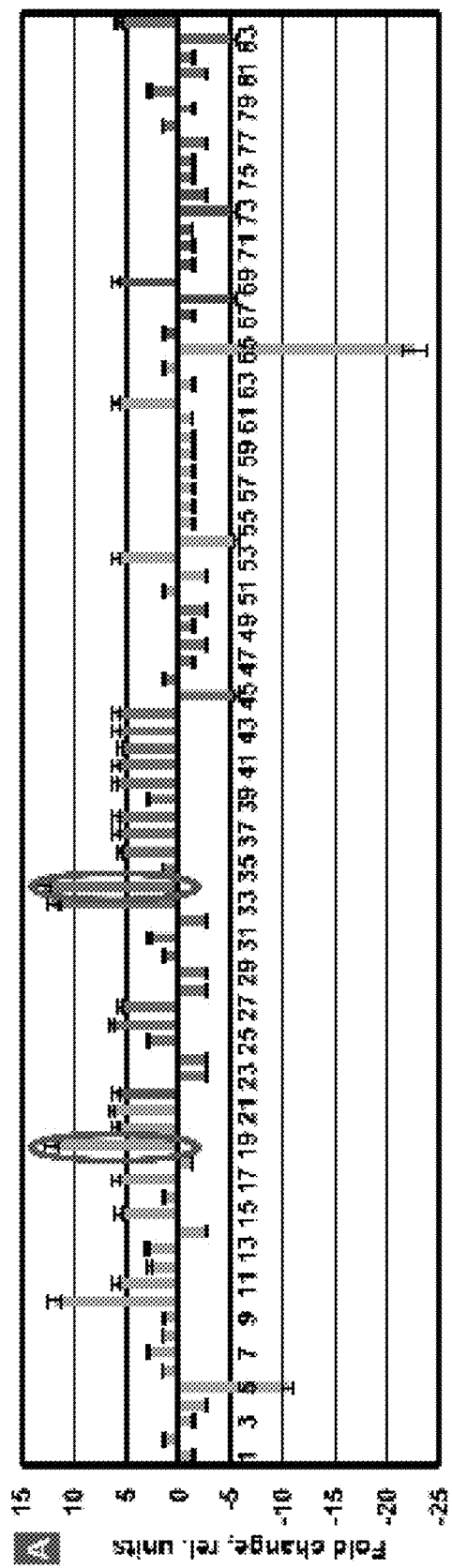
FIGS. 12A-B show gene expression measured by the Quantitative Polymerase Chain Reaction (QPCR) ((A) Mice instilled with bleomycin (1.5 U/kg); (B) Mice instilled with bleomycin (1.5 U/kg) and treated by inhalation with liposomal PGE2. Proteins chosen as targets for siRNA are selected (marked with red ellipse))
Figure 12B:
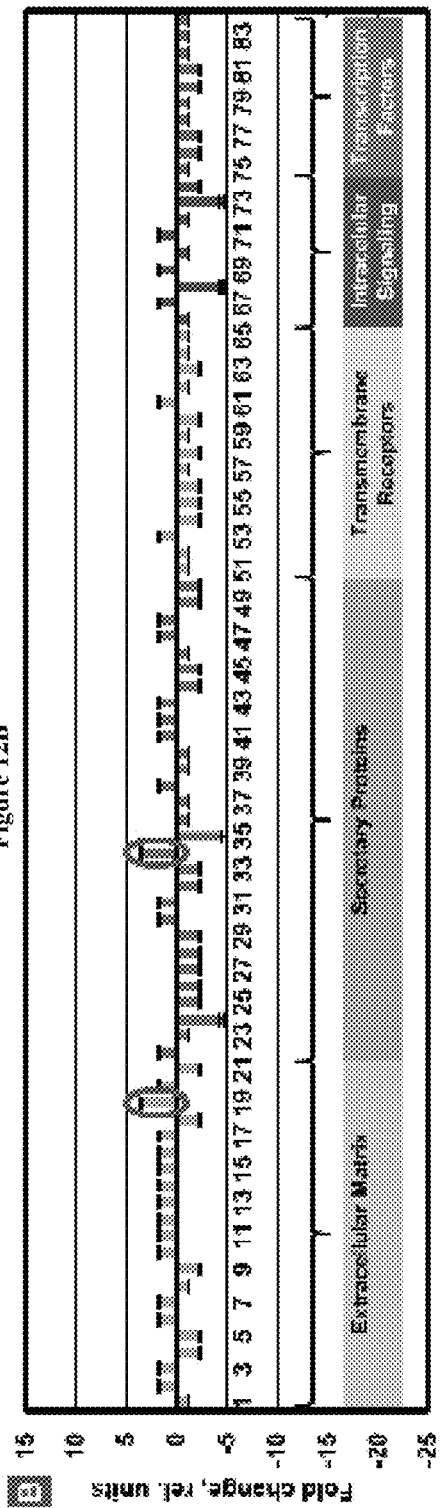

The profiles of the expression of 84 key genes involved in tissue remodeling during wound repair and development of fibrosis were studied in the lung tissues. The data obtained using the standard Mouse Fibrosis RT Profiler™ PCR Array panel showed that after instillation of bleomycin, 24 studied genes were upregulated by more than 5 times while 7 out of 84 genes were downregulated more than 5-fold (FIG. 12A). Overexpression of some proteins was confirmed using immunostaining of lung tissue sections (FIG. 13A). In addition to genes included in the mouse fibrosis array, the expression of VEGF and hypoxia inducible factor 1 alpha (HIF1A) proteins was analyzed by immunohistochemistry (FIG. 13A) and Western blotting (FIG. 13B). Instillation of bleomycin led to the overexpression of HIF1A protein (FIGS. 13A and B). Notably, the treatment of mice with liposomal PGE2 delivered by inhalation after instillation of bleomycin almost completely normalized the expression of the majority of studied genes (FIG. 12B). However, the expression of several genes and proteins was still substantially higher when compared with control after the treatment with PGE2: matrix metalloproteinase (MMP3, stromelysin, (FIG. 12B, #19; FIG. 13A), chemokine (CCL12, FIG. 12B, #34; FIG. 13A) and hypoxia inducible factor one alpha (HIF1A, FIGS. 13A and B). At the same time, signs of interstitial edema, inflammation, hypoxic damage, and high hydroxyproline content in the lungs were preserved after treatment with PGE2 alone. Consequently, the suppression of one or more mentioned proteins involved in the development of lung damage during IPF in combination with PGE2 enhance the treatment efficiency.

Discussion

Animals were inhaled with NLC contained PGE2 and/or siRNA targeted to HIF1A mRNA. The selected siRNA delivered by NLC into the lungs by inhalation alone or in combination with PGE2 significantly silenced the targeted HIF1A protein (FIG. 13B).

Inhalation of PGE2 in combination with siRNA targeted to HIF1A mRNA in one

NLC-based system led to the normalization of lung weight and substantial decrease in lung hydroxyproline content in animals with IPF (FIGS. 9 B and C). However, the signs of IPF and lung tissue injury detected by MRI (FIG. 9D) and histopathology (FIG. 9E) were substantially less pronounced after the treatment with PGE2 alone delivered locally into the lungs.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the presentinvention as defined by the following claims.

What is claimed is:

1. A composition comprising a plurality of lipid nanoparticles, wherein at least one lipid nanoparticle comprises:
   (i) a lipid membrane surrounding an inner compartment of the nanoparticle,
   (ii) an aqueous phase encapsulated by the inner compartment,
   (iii) an active ingredient contained within the lipid membrane of the nanoparticle, wherein the active ingredient is prostaglandins, and
   (iv) siRNA bound to the lipid nanoparticle via a cationic agent or bound to an outer lipid surface of the lipid nanoparticle via a disulfide bond,
   wherein each lipid nanoparticle has a diameter ranging from 1 nm to 1000 nm.

2. A composition comprising a plurality of lipid nanoparticles, wherein at least one lipid nanoparticle comprises:
   (i) a mixture of solid and liquid lipids and
   (ii) at least one lipid-soluble active agent contained within the lipid mixture, wherein the active agent is prostaglandins, and
   (iii) siRNA bound to the lipid nanoparticle via a cationic agent or bound to an outer lipid surface of the lipid nanoparticle via a disulfide bond,
   wherein each lipid nanoparticle has a diameter ranging from 1 nm to 1000 nm.

3. The composition of claim 1, wherein the active agent is prostaglandin E2.

4. The composition of claim 1, further comprising, in combination with the plurality of lipid nanoparticles, one or more pharmaceutical excipients selected from the group consisting of humectants, viscosity modifiers, surfactants, pH stabilizers, freeze drying protectants, polymers, and combinations thereof.

5. The composition of claim 2, further comprising, in combination with the plurality of lipid nanoparticles, one or more pharmaceutical excipients selected from the group consisting of humectants, viscosity modifiers, surfactants, pH stabilizers, freeze drying protectants, polymers, and combinations thereof.

6. The composition of claim 1, further comprising one or more additional ingredients contained within the lipid nanoparticle or bound to an outer lipid surface of the lipid nanoparticle, wherein the one or more additional ingredients are selected from the group consisting of anti-histaminic agents, anti-inflammatory agents, corticosteroids, nucleic acids, peptides, proteins, oligonucleotides, enzyme imaging agents, fluorescent dyes and combinations thereof.

7. The composition of claim 2, further comprising one or more additional ingredients contained within the lipid nanoparticle or bound to an outer lipid surface of the lipid nanoparticle, wherein the one or more additional ingredients are selected from the group consisting of anti-histaminic agents, anti-inflammatory agents, corticosteroids, nucleic acids, peptides, proteins, oligonucleotides, enzyme imaging agents, fluorescent dyes and combinations thereof.

8. The composition of claim 6, wherein the additional ingredient is a cyclooxygenase inhibitor.

9. The composition of claim 7, wherein the additional ingredient is a cyclooxygenase inhibitor.

10. The composition of claim 1, wherein the lipid nanoparticle further comprises 1,2-distearoyl-sn-glycero-3-phosphoethanolamine-N-[amino(polyethylene glycol) bound to an outer lipid surface of the lipid nanoparticle.

11. The composition of claim 2, wherein the lipid nanoparticle further comprises 1,2-distearoyl-sn-glycero-3-phosphoethanolamine-N-[amino(polyethylene glycol) bound to an outer lipid surface of the lipid nanoparticle.

12. The composition of claim 1, wherein the lipid nanoparticle further comprises cholesterol incorporated into the lipid membrane.

* * * * *